US008450300B2

(12) United States Patent
Jones

(10) Patent No.: US 8,450,300 B2
(45) Date of Patent: May 28, 2013

(54) FUSIDIC ACID DOSING REGIMENS FOR TREATMENT OF BACTERIAL INFECTIONS

(75) Inventor: Ronald Norman Jones, Silverton, OR (US)

(73) Assignee: Cempra Pharmaceuticals Inc., Chapel Hill, NC (US)

( * ) Notice: Subject to any disclaimer, the term of this patent is extended or adjusted under 35 U.S.C. 154(b) by 149 days.

(21) Appl. No.: 12/501,548

(22) Filed: Jul. 13, 2009

(65) Prior Publication Data

US 2011/0009375 A1 Jan. 13, 2011

(51) Int. Cl.
*A61K 31/56* (2006.01)

(52) U.S. Cl.
USPC ........................................................ 514/182

(58) Field of Classification Search
USPC ........................................................ 514/182
See application file for complete search history.

(56) References Cited

U.S. PATENT DOCUMENTS

| | | | |
|---|---|---|---|
| 2002/0142948 | A1 | 10/2002 | Oleson, Jr. et al. |
| 2004/0018234 | A1 | 1/2004 | Rudnic et al. |

OTHER PUBLICATIONS

Aarestrup, Antibacterial Resistance in Bacteria of Animal Origin, © 2006.*
Panagopoulos, P. et al, International Journal of Antimicrobial Agents, 2008, vol. 32, pp. 485-487.
Macgowan, A.P. et al, Journal of Antimicrobial Chemotherapy, 1989, vol. 23, pp. 409-415.
Taburet, A.M. et al, Journal of Antimicrobial Chemotherapy, 1990, vol. 25, Suppl. B, pp. 23-31.
International Search Report and Written Opinion for PCT/US09/50353, dated Mar. 31, 2010.
Verbist, L., The antimicrobial activity of fusidic acid, Journal of Antimicrobial Chemotherapy (1990) 25, Suppl. B, 1-5.
Bryskier, A., Ch. 23, Fusidic Acid in Antimicrobial Agents: Antibacterials and Antifungals, pp. 631-641 (2005).
Skov, Robert et al., Correlation of MIC methods and tentative interpretive criteria for disk diffusion susceptibility testing using NCCLS methodology for fusidic acid, Diagnostic Microbiology and Infectious Disease 40 (2001) 111-116.
Collignon, Peter et al., Fusidic acid in vitro activity, International Journal of Antimicrobial Agents 12 (1999) S45-S58.
Spelman, Denis, Fusidic acid in skin and soft tissue infections, International Journal of Antimicrobial Agents 12 Suppl. 2 (1999) S59-S66.
Mandell et al., Principles and Practice of Infectious Diseases, 6th edition, vol. 1, Oct. 13, 2006.
Ernst, Jorgen, Fucidin Treatment of Chronic *Staphylococcal* Osteitis and Osteomyelitis, Acta Orthop. Scand. 1969, 40(5):677.
Hierholzer, G. et al., Antibiotic Therapy of Chronic Post-Traumatic Osteomyelitis, J. Bone Joint Surg. vol. 56 B, No. 4, Nov. 1974, pp. 721-729.
Lautenbach, E.E.G. et al., Serum and Tissue Concentrations of Sodium Fusidate in Patients With Chronic Osteomyelitis and in Normal Volunteers, South African Journal of Surgery, vol. 13, No. 1, Mar. 1975, pp. 21-32.
Pahle, Jan A., Experiences with Fucidin in the Treatment of Osteomyelitis, Acta Orthop. Scand. 1969, 40(5):675.
Saggers, B.A. et al., Serum Levels with Sodium Fusidate, The British Journal of Clinical Practice, vol. 22, Issue 10, 1968, pp. 429-430.
Schumer, William et al., Sodium Fusidate in Surgical Wound Infections, American Journal of Surgery, vol. 115, Apr. 1968, pp. 527-530.
Török, Eva et al., Fusidic acid suspension twice daily: a new treatment schedule for skin and soft tissue infection in children, with improved tolerability, Journal of Dermatological Treatment (2004) 15, 158-163.
Nordin, P. et al., A comparison of fusidic acid and flucloxacillin in the treatment of skin and soft-tissue infection, European Journal of Clinical Research 1994; 5:97-106.
Christiansen, Keryn, Fusidic acid adverse drug reactions, International Journal of Antimicrobial Agents 12 (1999) S3-S9.
Coutant, Christiane et al., Disk Diffusion Interpretive Criteria for Fusidic Acid Susceptibility Testing of *Staphylococci* by the National Committee for Clinical Laboratory Standards Method, Diagn Microbiol Infect Dis 1996;25:9-13.
Reeves, D.S., Review The pharmacokinetics of fusidic acid, Journal of Antimicrobial Chemotherapy (1987) 20, 467-476.
Turnidge, John, Fusidic acid pharmacology, pharmacokinetics and pharmacodynamics, International Journal of Antimicrobial Agents 12 (1999) S23-S34.
Vaillant, L. et al., Levels of fusidic acid in skin blister fluid and serum after repeated administration of two dosages (250 and 500 mg), British Journal of Dermatology (1992) 126, 591-595.
Munkholm, P. et al, Antibiotic activity in serum following single and repeated oral administration of sodium fusidate in volunteers, European Journal of Drug Metabolism and Pharmacokinetics, 1994, vol. 19, No. 4, pp. 337-341.
Guttler, F. et al., Interaction of albumin and fusidic acid, Br. J. Pharmac. (1971), 43, 151-160.
Rieutord, A. et al., In vitro study of the protein binding of fusidic acid: a contribution to the comprehension of its pharmacokinetic behaviour, International Journal of Pharmaceutics 119(1995) 57-64.
Taburet, A.M. et al., Pharmacokinetics of sodium fusidate after signal and repeated infusions and oral administration of a new formulation, Journal of Antimicrobial Chemotherapy (1990) 25, Suppl. B, 23-31.
Evans, R.J. et al., Naturally-occurring fusidic acid resistance in *staphylococci* and its linkage to other resistances, J. Clin. Path. (1966), 19, 555-560.
Hansson, Sebastian et al., Structural Insight into Fusidic Acid Resistance and Sensitivity in EF-G, J. Mol. Biol. (2005) 348, 939-949.
Jensen, K.A. et al., Fucidin A Study on Problems of Resistance. I., Acta Path. Microbiol. Scand. 60(2):271-284 (1964).

(Continued)

*Primary Examiner* — Frederick Krass
*Assistant Examiner* — Adam C Milligan
(74) *Attorney, Agent, or Firm* — Roylance, Abrams, Berdo & Goodman, L.L.P.

(57) ABSTRACT

Novel dosing regimens for the treatment and prevention of bacterial infections using fusidic acid are described. The use of a high loading dose of fusidic acid, followed by moderate maintenance doses of the drug, have been found to prevent development of drug-resistant strains of bacteria, to increase the effective spectrum of the drug, and to avoid nausea and vomiting associated with a prolonged course of therapy of high amounts of the drug.

75 Claims, 8 Drawing Sheets

OTHER PUBLICATIONS

Besier, Silke et al., Compensatory Adaptation to the Loss of Biological Fitness Associated with Acquisition of Fusidic Acid Resistance in *Staphylococcus aureus*, Antimicrobial Agents and Chemotherapy, 2005, 49(4):1426-1431.

Gemmell, Curtis G. et al, Guidelines for prophylaxis and treatment of methicillin-resistant *Staphylococcus aureus* (MRSA) infections in the UK, Journal of Antimicrobial Chemotherapy (2006) 57, 589-608.

O'Neill, Alex J. et al., Mutation frequencies for resistance to fusidic acid and rifampicin in *Staphylococcus aureus*, Journal of Antimicrobial Chemotherapy (2001) 47, 647-650.

Howden, Benjamin P. et al., Dumb and Dumber—The Potential Waste of a Useful Antistaphylococcal Agent: Emerging Fusidic Acid Resistance in *Staphylococcus aureus*, Clinical Infect. Dis 2006, 42:394-400.

Gould, F. Kate et al. Guidelines (2008) for the prophylaxis and treatment of methicillin-resistant *Staphylococcus aureus* (MRSA) infections in the United Kingdom, Journal of Antimicrobial Chemotherapy (2009) 63, 849-861.

Lannergard, Jonas et al., Genetic Determinants of Resistance to Fusidic Acid among Clinical Bacteremia Isolates of *Staphylococcus aureus*, Antimicrobial Agents and Chemotherapy, May 2009, 53(5):2059-2065.

Machet, L. et al., Treatment of skin infections with two dosages of fusidic acid (500 mg/day and 1 g/day) compared with pristinamycin 2 g/day: a multicenter randomised study, Nouv. Dermatol., 1994: 13:520-524, Abstract only.

Brodersen, R., Fusidic acid binding to serum albumin and interaction with binding of bilirubin, Acta Paediatr Scand. Nov. 1985;74(6):874-880.

von Daehne, W, et al., Structure-Activity Relationships in Fusidic Acid-Type Antibiotics, Advances in Applied Microbiology, 25:95-146 1979.

Schmid, J. et al., Fucidic acid in Gunn rats. No influence on serum bilirubin concentration. Arch Dis Child., Jul. 1979;54(7):566-567.

Pfaller, M.A. et al., Evaluation of the activity of fusidic acid tested against contemporary Gram-positive clinical isolates from the USA and Canada. Int J Antimicrob Agents. 35(3):282-7 (2010).

van Bijsterveld, Fusidic acid in infections of the external eye, Infection 15(1):16-9 (1987).

Carr, WD et al. Fusidic acid tablets in patients with skin and soft-tissue infection: a dose-finding study. Eur J Clin Res. 1994;5:87-95.

Rolinson, GN et al., The binding of antibiotics to serum proteins, Br J Pharmacol Chemother, Dec. 1965;25 (3):638-650.

Schuirmann, DJ, A comparison of the two one-sided tests procedure and the power approach for assessing the equivalence of average bioavailability, J Pharmacokinet Biopharm., 1987: 15(6):657-680.

Okusanya, O.O., et al. CEM-102 (Sodium Fusidate) Dosage regimen decision support using population pharmacokinetic (PPK) and mechanism-based pharmacokinetic-pharmacodynamic (PK-PD) models. Abstract 1245. 47th Annual Meeting of the Infectious Diseases Society of America, Philadelphia, PA, Oct. 29-Nov. 1, 2009.

Tsuji, B.T., et al. Pharmacokinetics-Pharmacodynamics (PK-PD) of CEM-102 (Sodium Fusidate) Against *Streptococcus pyogenes* Using In Vitro Pharmacodynamic Models (IVPM). Abstract A1-021. 50th Interscience Conference on Antimicrobial Agents and Chemotherapy, Boston, MA, Sep. 12-15, 2010.

Kosowska-Shick, K., P. McGhee, L. Beachel, P.C. Appelbaum. Ability of CEM-102 (Fusidic Acid), Linezolid, Daptomycin to Select Resistant *S.aureus* Mutants at Steady-state Plasma Levels. Abstract E-1557. 50th Interscience Conference on Antimicrobial Agents and Chemotherapy, Boston, MA, Sep. 12-15, 2010.

Bulitta, J.B., et al. Population Pharmacokinetics (PPK) of CEM-102 in Healthy Subjects. Abstract A1-1932. 49th Interscience Conference on Antimicrobial Agents and Chemotherapy, San Francisco, CA, Sep. 12-15, 2009.

Castanheira, M., et al. CEM-102 (Fusidic Acid) in vitro activity and evaluation of molecular resistance mechanisms among European Gram-positive isolates (2008-2009). Abstract 929. 20th European Society of Clinical Microbiology and Infectious Diseases, Vienna, Austria, Apr. 10-13, 2010.

Tsuji, B.T., et al. Pharmacokinetics-Pharmacodynamics (PK-PD) of CEM-102 against Methicillin-resistant *Staphylococcus aureus* (MRSA) using an in vitro PD model (IVPM) and mechanism-based (MB) modeling. Abstract A1-1933. 49th Interscience Conference on Antimicrobial Agents and Chemotherapy, San Francisco, CA, Sep. 12-15, 2009.

Still, J.G., et al. Pharmacokinetics and safety of single, multiple, and loading doses of CEM-102 in healthy subjects. Abstract A1-1931. 49th Interscience Conference on Antimicrobial Agents and Chemotherapy, San Francisco, CA, Sep. 12-15, 2009.

* cited by examiner

FUSIDIC ACID DOSING REGIMENS FOR TREATMENT OF BACTERIAL INFECTIONS

BACKGROUND OF THE INVENTION

Fusidic acid (FA) is a tetracyclic triterpenoid or fusidane (steroidal) antibiotic derived from the fungus *Fusidium coccineum* that inhibits bacterial protein synthesis. FA is effective against gram-positive bacteria such as *Staphylococcus* species and *Corynebacterium* species (L. Verbist, *J. Antimicro. Chemo.* 25, Suppl. B, 1-5 (1990); A. Bryskier, Fusidic Acid, Chapter 23, in *Antimicrobial Agents: Antibacterials and Antifungals* (Andre Bryskier, Ed., ASM Press, Washington, USA, 2005)). FA also has moderate activity against Group A beta-hemolytic streptococci, or *Streptococcus pyogenes* (L. Verbist, *J. Antimicro. Chemo.* 25, Suppl. B, 1-5 (1990); A. Bryskier, Fusidic Acid, Chapter 23, in *Antimicrobial Agents: Antibacterials and Antifungals* (Andre Bryskier, Ed., ASM Press, Washington, USA, 2005); Skov et al., *Diag. Micro. Infect. Dis.* 40:111-116 (2001)).

FA was developed for clinical use in the 1960s and it is approved for human use outside of the United States, such as in the UK, Canada, Europe, Israel, Australia and New Zealand. It is typically prescribed at doses of 500 mg TID for treating skin and skin structure infections caused by *Staphylococcus aureus* (A. Bryskier, Fusidic Acid, Chapter 23, in *Antimicrobial Agents: Antibacterials and Antifungals* (Andre Bryskier, Ed., ASM Press, Washington, USA, 2005); Collignon et al., *Int'l J. Antimicrobial Agents* 12:S45-S58 (1999); D. Spelman, *Int'l J. Antimicrobial Agents* 12:S59-S66 (1999)), although some physicians have routinely prescribed the compound at 500 mg BID for treating skin and skin structure infections due to the long half-life of the compound (Fusidic Acid, in *Principles and Practice of Infectious Diseases*, 6$^{th}$ ed. (Mandell et al. eds., Elsevier, 2006)).

Treatment using FA has been well studied and it is generally regarded as safe when administered to humans, as evidenced by the fact that the drug has been in continuous use for more than 40 years. There are, however, several characteristics of FA that have prevented use of the drug against a wider spectrum of bacteria and in the treatment in additional types of infection. For example, approved dosing regimens have been shown to select for bacterial resistance, such as in *S. aureus*. Approved dosing regimens provide low multiples of the MIC and as a result, *S. aureus* resistant mutants can be selected after the first day of dosing. Once resistance has developed, FA is not effective against the resistant strains. Resistance is reported to occur if FA is used as a single drug as the resistance frequency at 4 and 8 times the MIC is in the range of $10^{-6}$ or $10^{-8}$ (Evans et al., *J. Clin. Path.* 19:555-560 (1966); Hansson et al., *J. Mol. Biol.* 348:939-949 (2005), Jensen et al., *Acta Pathol Microbiol Scand.* 60:271-284 (1964); Besier et al., *Antimicrob. Agents Chemo.*, 49(4):1426-1431 (2005); Gemmell et al., *J. Antimicrobial Chemo.* 57:589-608 (2006)).

The dosage of the drug cannot be simply increased as a means of avoiding development of resistance. It is difficult to achieve high concentrations of FA in the blood due to the substantial protein binding of the drug (approximately 95-97%) (K. Christiansen, International Journal of Antimicrobial Agents 12:S3-S9 (1999); Coutant et al., *Diagn Microbiol Infect Dis* 25:9-13 (1996); D. Reeves, *J. Antimicrob. Chemo.* 20:467-476 (1987); J. Turnidge, *Int'l J. Antimicrobial Agents* 12:S23-S34 (1999); Rieutord et al., Int'l J. Pharmaceutics 119:57-64 (1995)). Moreover, high dosages of FA are not well-tolerated by patients receiving the drug. High doses of FA (e.g., 1 gram TID) are required if the drug is to be used in the treatment of bone and joint infections, less susceptible bacteria and other serious infections. However, treatment regimens using high doses of the drug induce nausea and vomiting and are rejected by patients (Fusidic Acid, in *Principles and Practice of Infectious Diseases*, 6$^{th}$ ed. (Mandell et al. eds., Elsevier, 2006); K. Christiansen, International Journal of Antimicrobial Agents 12:S3-S9 (1999); Nordin et al., *Eur. J. Clin. Res.* 5:97-106 (1994)).

In view of the tremendous costs associated with the de novo development of new anti-bacterials, expanding the indications for drugs that have already been demonstrated to be safe and effective is strongly needed. Overcoming the limitations on the uses of FA would broaden the population of bacterial infections against which it could be used and thus meet this need.

BRIEF SUMMARY OF THE INVENTION

According to a first embodiment, the present invention is directed to a method of treating or preventing a bacterial infection in a subject comprising:

(a) administering at least one loading dose of a pharmaceutical composition comprising fusidic acid, or a pharmaceutically acceptable salt thereof, to a subject in need of treatment or prevention, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 24 hours and a minimum trough plasma concentration of fusidic acid of not less than about 50 ug/ml, and (b) administering at least one maintenance dose of a pharmaceutical composition comprising fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

In a preferred aspect of the first embodiment, the $C_{max}$ is not less than about 80 ug/ml, the minimum trough plasma concentration of (a) is not less than about 60 ug/ml and the minimum trough plasma concentration of (b) is not less than about 70 ug/ml. In a further preferred aspect, the $C_{max}$ is not less than about 100 ug/ml, the minimum trough plasma concentration of (a) is not less than about 80 ug/ml and the minimum trough plasma concentration of (b) is not less than about 80 ug/ml.

In preferred aspects with regard to the loading dose, the loading dose comprises two loading doses, wherein the second loading dose is administered about 12 hours after administration of the first loading dose, and wherein each loading dose is between about 1000 mg and about 1850 mg. In further preferred aspects, the total loading dose administered to the subject is between about 2000 mg and about 3600 mg.

In preferred aspects with regard to the maintenance dose, the maintenance dose comprises multiple maintenance doses of independently between about 500 mg and 1000 mg, administered about 12 hours apart, beginning about 12 hours after administration of the loading dose.

In preferred aspects with regard to the minimum trough plasma concentration, a minimum trough plasma concentration of not less than about 50 ug/ml is maintained for at least about 48 hours after administering of the loading dose. More preferably, a minimum trough plasma concentration of not less than about 50 ug/ml is maintained for at least about 72 hours. Even more preferably, a minimum trough plasma concentration of not less than about 50 ug/ml is maintained for at least about 96 hours.

In a preferred aspect of the first embodiment, the loading dose comprises two loading doses, wherein each loading dose is independently between about 1000 mg and about 1850 mg, and wherein the second loading dose is administered about 12 hours after administration of the first loading dose; and the maintenance dose comprises multiple maintenance doses of independently between about 500 mg and 1000 mg administered about 12 hours apart, beginning about 12 hours after administration of the second loading dose. Preferably, each loading dose is independently at least about 1500 mg. Also preferably, each maintenance dose is independently at least about 600 mg.

In preferred aspects with regard to the subject, the subject is a human.

In preferred aspects with regard to the bacterial infection, the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. Preferably, the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*. In particular aspects, the bacterial infection is an infection caused by *Enterococcus faecalis* or *Enterococcus faecium*.

In other preferred aspects with regard to the bacterial infection, the bacterial infection is an infection selected from the group consisting of a skin and soft tissue infection, a bone infection, a joint infection, pneumonia, a wound infection, a burn infection, an infection of the blood, and an infection associated with cystic fibrosis.

In preferred aspects with regard to the pharmaceutical composition comprising fusidic acid, or a pharmaceutically acceptable salt thereof, the pharmaceutical composition is in the form of a tablet, a capsule, an IV solution, an inhalable formulation, a powder formulation, or a formulated suspension. Preferably, the pharmaceutical composition is administered orally, by injection or by intravenous infusion.

In another preferred aspect of the first embodiment, the subject does not experience an adverse level of nausea.

According to a second embodiment, the present invention is directed to a method of treating or preventing a bacterial infection in a subject comprising:

(a) administering at least one loading dose of a pharmaceutical composition comprising fusidic acid, or a pharmaceutically acceptable salt thereof, to a subject in need of treatment or prevention in an amount sufficient to achieve a minimum plasma concentration of not less than about 50 ug/ml fusidic acid within 24 hours, and (b) administering at least one maintenance dose of a pharmaceutical composition comprising fusidic acid, or a pharmaceutically acceptable salt thereof, to the subject of (a) in an amount sufficient to maintain a minimum plasma concentration of not less than about 50 ug/ml fusidic acid for at least about 24 hours after the administering of (a).

In a preferred aspect of the second embodiment, a minimum plasma concentration of fusidic acid of not less than about 60 ug/ml is achieved in (a) and a minimum plasma concentration of fusidic acid of not less than about 60 ug/ml is maintained in (b). In a further preferred aspect, a minimum plasma concentration of fusidic acid of not less than about 80 ug/ml is achieved in (a) and a minimum plasma concentration of fusidic acid of not less than about 80 ug/ml is maintained in (b).

In preferred aspects with regard to the loading dose, the loading dose comprises two loading doses, wherein the second loading dose is administered about 12 hours after the first loading dose, and wherein each loading dose is between about 1000 mg and about 1850 mg. In further preferred aspects, the total loading dose administered to the subject is between about 2000 mg and about 3600 mg.

In preferred aspects with regard to the maintenance dose, the maintenance dose comprises multiple maintenance doses of independently between about 500 mg and 1000 mg administered about 12 hours apart, beginning about 12 hours after administration of the loading dose.

In preferred aspects with regard to the minimum plasma concentration, a minimum plasma concentration of not less than about 50 ug/ml is maintained for at least about 48 hours after administering the loading dose, preferably a minimum plasma concentration of not less than about 50 ug/ml is maintained for at least about 72 hours, more preferably, a minimum plasma concentration of not less than about 50 ug/ml is maintained for at least about 96 hours.

In a preferred aspect of the second embodiment, the loading dose comprises two loading doses, wherein each loading dose is independently between about 1000 mg and about 1850 mg, and wherein the second loading dose is administered about 12 hours after administration of the first loading dose; and multiple maintenance doses of independently between about 500 mg and 1000 mg are administered, about 12 hours apart, beginning about 12 hours after administration of the second loading dose. Preferably, each loading dose is independently at least about 1500 mg. Equally preferably, each maintenance dose is independently at least about 600 mg.

In preferred aspects with regard to the subject, the subject is a human.

In preferred aspects with regard to the bacterial infection, the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. Preferably, the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus,*

*Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*. In particular aspects, the bacterial infection is an infection caused by *Enterococcus faecalis* or *Enterococcus faecium*.

In further preferred aspects with regard to the bacterial infection, the bacterial infection is an infection selected from the group consisting of a skin and soft tissue infection, a bone infection, a joint infection, pneumonia, a wound infection, a burn infection, an infection of the blood, and an infection associated with cystic fibrosis.

In preferred aspects with regard to the pharmaceutical composition comprising fusidic acid, or a pharmaceutically acceptable salt thereof, the pharmaceutical composition is in the form of a tablet, a capsule, an IV solution, an inhalable formulation, a powder formulation, or a formulated suspension. Preferably, the pharmaceutical composition is administered orally, by injection or by intravenous infusion.

In another preferred aspect of the second embodiment, the subject does not experience an adverse level of nausea.

According to a third embodiment, the present invention is directed to a method of treating or preventing a bacterial infection in a subject comprising:

(a) administering a first and a second loading dose of a pharmaceutical composition comprising fusidic acid, or a pharmaceutically acceptable salt thereof, to a subject in need of treatment or prevention, wherein each loading dose is independently between about 1000 mg and about 1850 mg, and wherein the second loading dose is administered about 12 hours after administration of the first loading dose; and (b) administering two or more maintenance doses of a pharmaceutical composition comprising fusidic acid, or a pharmaceutically acceptable salt thereof, to the subject of (a), wherein each maintenance dose is independently between about 500 mg and 1000 mg, wherein a first maintenance dose is administered about 12 hours after administration of the second loading dose, and wherein subsequent maintenance doses are administered about 12 hours apart.

In a preferred aspect of the third embodiment, each loading dose is independently at least about 1500 mg.

In a further preferred aspect of the third embodiment, each maintenance dose is independently at least about 600 mg. In related aspects, at least three, four, five or six maintenance doses are administered to the subject.

In a preferred aspect with regard to the subject, the subject is a human.

In a preferred aspect with regard to the bacterial infection, the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. Preferably, the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysga-lactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*. In particular aspects, the bacterial infection is an infection caused by *Enterococcus faecalis* or *Enterococcus faecium*.

In an additional preferred aspect with regard to the bacterial infection, the bacterial infection is an infection selected from the group consisting of a skin and soft tissue infection, a bone infection, a joint infection, pneumonia, a wound infection, a burn infection, an infection of the blood, and an infection associated with cystic fibrosis.

In a preferred aspect with regard to the pharmaceutical composition comprising fusidic acid, or a pharmaceutically acceptable salt thereof, the pharmaceutical composition is in the form of a tablet, a capsule, an IV solution, an inhalable formulation, a powder formulation, or a formulated suspension. In a related aspect, the pharmaceutical composition is preferably administered orally, by injection or by intravenous infusion to the subject.

In another preferred aspect of the third embodiment, the subject does not experience an adverse level of nausea.

According to a fourth embodiment, the present invention is directed to a method of reducing development of an antibiotic-resistant strain of bacteria in a subject having a bacterial infection comprising:

(a) administering at least one loading dose of a pharmaceutical composition comprising fusidic acid, or a pharmaceutically acceptable salt thereof, to a subject having a bacterial infection, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 20 hours and a minimum trough plasma concentration of fusidic acid of not less than about 50 ug/ml, and (b) administering at least one maintenance dose of a pharmaceutical composition comprising fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

In a preferred aspect of the fourth embodiment, the $C_{max}$ is not less than about 80 ug/ml, the minimum trough plasma concentration of (a) is not less than about 60 ug/ml, and the minimum trough plasma concentration of (b) is not less than about 70 ug/ml. In a further preferred aspect, the $C_{max}$ is not less than about 100 ug/ml, the minimum trough plasma concentration of (a) is not less than about 80 ug/ml and the minimum trough plasma concentration of (b) is not less than about 80 ug/ml.

In preferred aspects with regard to the loading dose, the loading dose comprises two loading doses, wherein the second loading dose is administered about 12 hours after the first loading dose, and wherein each loading dose is between about 1000 mg and about 1850 mg. In further preferred aspects, the total loading dose administered to the subject is between about 2000 mg and about 3600 mg.

In a preferred aspect of the fourth embodiment, the loading dose comprises two loading doses, wherein the second loading dose is administered about 12 hours after the first loading dose, and wherein each loading dose is between about 1000 mg and about 1850 mg.

In another preferred aspect of the fourth embodiment, the maintenance dose comprises multiple maintenance doses of independently between about 500 mg and 1000 mg administered about 12 hours apart, beginning about 12 hours after administration of the loading dose.

In preferred aspects with regard to the minimum trough plasma concentration, a minimum trough plasma concentration of not less than about 50 ug/ml is maintained for at least about 48 hours after administering the loading dose, more preferably a minimum trough plasma concentration of not less than about 50 ug/ml is maintained for at least about 72 hours, even more preferably a minimum trough plasma concentration of not less than about 50 ug/ml is maintained for at least about 96 hours.

In a further preferred aspect of the fourth embodiment, the loading dose comprises two loading doses, wherein each loading dose is independently between about 1000 mg and about 1850 mg, and wherein the second loading dose is administered about 12 hours administration of after the first loading dose; and multiple maintenance doses of independently between about 500 mg and 1000 mg are administered to the subject about 12 hours apart, beginning about 12 hours after administration of the second loading dose. Preferably, each loading dose is independently at least about 1500 mg. Equally preferably, each maintenance dose is independently at least about 600 mg.

In preferred aspects with regard to the subject, the subject is a human.

In preferred aspects with regard to the infection, the bacterial infection is caused by a bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. Preferably, the infection is caused by a bacteria selected from the group consisting of *Staphylococcus aureus* (methicillin-resistant and -susceptible), *Staphylococus epidermidis*, *Staphylococus hemolyticus*, *Staphylococus saprophyticus*, *Staphylococus lugdunensis*, *Staphylococus capitis*, *Staphylococus caprae*, *Staphylococus saccharolyticus*, *Staphylococus simulans*, *Staphylococus warneri*, *Staphylococus hominis*, *Staphylococus intermedius*, *Staphylococus pseudointermedius*, *Staphylococus lyricus*, *Streptococcus pyogenes*, *Streptococcus agalactiae*, *Streptococcus dysgalactiae* subspecies *dysgalactiae*, *Streptococcus anginosus*, *Streptococcus mitis*, *Streptococcus salivarius*, *Streptococcus bovis*, *Streptococcus mutans*, *Neisseria gonorrhoeae*, *Neisseria meningitidis*, *Bacillus anthracis*, *Bordetella pertussis*, *Clostridium difficile*, *Enterococcus faecalis*, *Enterococcus faecium* and *Corynebacterium diphtheriae*. In particular aspects, the infection is caused by *Enterococcus faecalis* or *Enterococcus faecium*.

DETAILED DESCRIPTION OF THE INVENTION

Figure 1:
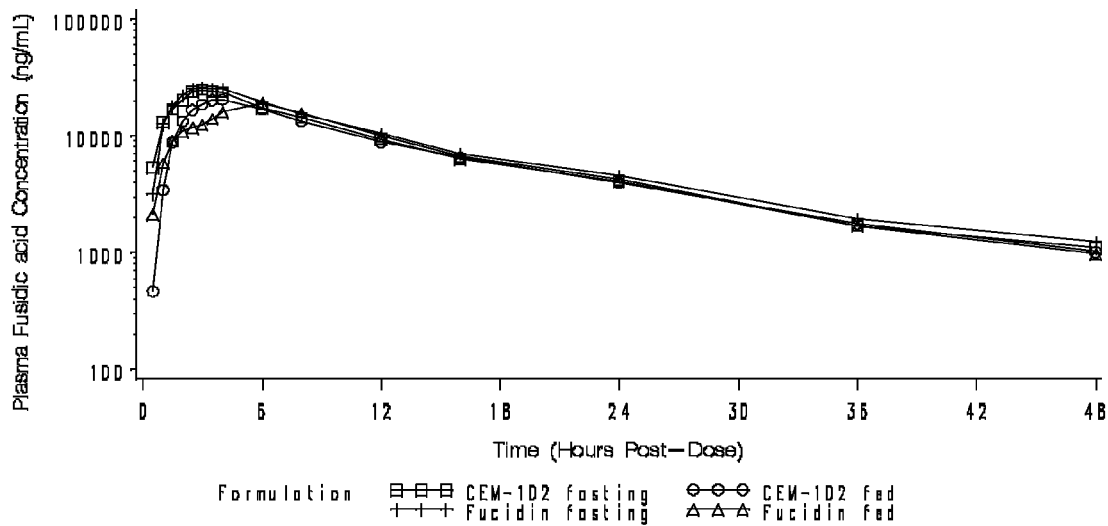
FIG. 1—Mean plasma concentrations of fusidic acid after a single dose of sodium fusidate (semi-log plot).

Conventional treatment using FA is problematic due to the fact that while low doses of the drug result in the selection of drug-resistant organisms, higher optimal doses are not possible due to severe nausea and vomiting induced in subjects. This has resulted in the dogma that monotherapy results in resistance and combination therapy is required to defeat resistance selection.

Through numerous studies and the diligent efforts of the inventors, and as disclosed herein, it has been discovered that both problems associated with conventional FA therapy can be avoided by administering to a subject a high (loading) dose of FA during the first day of treatment, and a moderate (maintenance) dose of FA on succeeding days of treatment. The loading dose is of sufficient amount that at least a 2-fold excess, and in some cases at least a 10-fold excess, of the drug above the MIC of the bacterial infection being treated or inhibited, is administered to the subject on the first day of treatment. By administering a large amount of the drug to the subject within the first day of treatment, a high plasma concentration of the drug can be reached within a short period of time. Quickly reaching a maximum plasma concentration ($C_{max}$) that is well above the MIC for the bacterial infection that is being treated or prevented prevents development of FA-resistance in the bacteria.

Limiting the administration of high doses of FA to the loading phase (the first day of treatment), and decreasing the dosage(s) given to the subject on the second and succeeding days of treatment (the maintenance phase), avoids the severe nausea and vomiting seen when large amounts of FA are administered for prolonged periods of time. The doses given during the maintenance phase are sufficient to maintain a minimum trough plasma concentration of FA for sufficient time in which to treat or prevent the bacterial infection, but not so great as to cause an unacceptable degree of nausea or to induce vomiting.

As an example, and as further discussed in the Examples below, a loading dose regimen of 1100 mg BID FA for the first day, followed by 550 mg BID FA for five days as the maintenance dose, showed that the drug was well tolerated and that a trough level of at least 74 ug/ml in the plasma was achieved, much higher than the MIC of 2.5 ug/ml of *S. aureus* in humans.

The use of a high loading dose and moderate maintenance doses has the added benefit of expanding the number species of bacteria against which FA can be used in treatment.

According, the present invention is directed to methods for treating or preventing bacterial infections in a subject. The methods are based on the novel dosing regimens disclosed herein.

In each of the methods of the present invention, the novel dosing regimens comprise two phases, a loading dose phase followed by a maintenance dose phase.

Loading Dose

The loading dose phase is the period of time over which a high dose of FA is administered to a subject. By administering a high dose of FA to the subject over a short period of time, the development of drug-resistant strains of bacteria can be avoided.

In one embodiment of the invention, the loading dose phase is defined by the administration of fusidic acid to a subject in an amount sufficient to reach a pharmacokinetic (PK) profile for fusidic acid defined by three variables: (i) a maximum plasma concentration ($C_{max}$), (ii) a time to maximum plasma concentration ($T_{max}$) of fusidic acid, and (iii) a minimum trough plasma concentration of fusidic acid. With regard to the first variable, the maximum plasma concentration ($C_{max}$) of fusidic acid is not less than about 50, 55, 60, 65, 70, 75, 80, 85, 90, 95, 100, 105, 110, 115 or 120 ug/ml, or a value within this range, preferably not less than about 80 ug/ml, more preferably not less than about 100 ug/ml. With regard to the second variable, the time to maximum plasma concentration ($T_{max}$) of fusidic acid is no more than about 12, 13, 14, 15, 16, 17, 18, 19, 20, 21, 22, 23, 24, 25, 26, 27, 28, 29 or 30 hours, preferably no more than about 24 hours. With regard to the third variable, the minimum trough plasma concentration of fusidic acid is not less than about 40, 45, 50, 55, 60, 65, 70, 75, 80, 85, 90, 95 or 100 ug/ml, or a value within this range, preferably not less than about 60 ug/ml, more preferably not less than about 80 ug/ml.

The loading dose administered to the subject may also be defined based on the amount of FA sufficient to achieve a minimum plasma concentration within a particular period of time. The minimum plasma concentration of fusidic acid is not less than about 40, 45, 50, 55, 60, 65, 70, 75, 80, 85, 90, 95 or 100 ug/ml, or a value within this range, preferably not less than about 60 ug/ml, more preferably not less than about 80 ug/ml. The period of time in which the minimum plasma concentration of fusidic acid is achieved is within about 12, 13, 14, 15, 16, 17, 18, 19, 20, 21, 22, 23, 24, 25, 26, 27, 28, 29 or 30 hours, preferably within about 24 hours. In preferred aspects, the loading dose of fusidic acid is an amount sufficient to achieve a minimum plasma concentration of not less than about 50 ug/ml fusidic acid within about 24 hours of administration the subject.

The skilled artisan will understand that as long as the particular PK profile or minimum plasma concentration is achieved, the loading dose may be split into discrete loading doses that are administered to a subject over a particular period of time. Therefore, in addition to a single loading dose, the loading dose may comprise two, three, four, five, six or more discrete loading doses. The total amount of FA administered to a subject as the loading dose is about 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000 mg or more of FA, or a value within this range. Preferably, the total loading dose is between about 2000 mg and 3600 mg of FA. Where two or more discrete loading doses are administered to a subject, the skilled artisan will understand that any fraction of the total loading dose may be used in each discrete loading dose, whether the discrete doses are equal in concentration or unequal (e.g., two-thirds of the total loading dose in a first dosage, and one-third of the total loading dose in a second dosage). In a preferred aspect, the loading dose is administered to a subject as two discrete loading doses, where each discrete loading dose is about 1000, 1100, 1200, 1300, 1400, 1500, 1600, 1700, 1800 or 1850 mg, or a value within this range. Preferably, each loading dose is between about 1000 mg and 1850 mg of FA With regard to the period of time over which the loading dose is administered to the subject, the skilled artisan will understand that quickly reaching a desired $C_{max}$ or a particular minimum plasma concentration is important to avoid development of FA-resistant strains of bacteria. However, the entirety of the loading dose will be administered to the subject within about 6, 7, 8, 9, 10, 11, 12, 13, 14, 15, 16, 17, 18, 19, 20, 21, 22, 23, 24 or more hours. In a preferred aspect, the entirety of the loading dose will be administered to the subject within about 20 hours. When the loading dose is split into two or more discrete loading doses, the time periods between administrations of the discrete loading doses may be equal or unequal. Preferably, the time periods are equal.

The loading dose administered to the subject may further be defined simply based on the amount of FA administered to the subject. The total amount of FA administered to a subject as the loading dose may be about 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000 mg or more of FA, or a value within this range. Preferably, the total loading dose is between about 2000 mg and 3600 mg of FA. As above, the loading dose may be split into discrete loading doses that are administered to a subject over a particular period of time, such as two, three, four, five, six or more discrete loading doses. Where two or more discrete loading doses are administered to a subject, any fraction of the total loading dose may be used in each discrete loading dose, whether the discrete doses are equal in concentration or unequal (e.g., two-thirds of the total loading dose in a first dosage, and one-third of the total loading dose in a second dosage). In a preferred aspect, the loading dose is administered to a subject as two discrete loading doses, where each discrete loading dose is about 1000, 1100, 1200, 1300, 1400, 1500, 1600, 1700, 1800 or 1850 mg, or a value within this range.

In preferred aspects, the loading dose is administered to a subject as two discrete loading doses, where each discrete loading dose is about 1000 mg, and where in the second loading dose is administered about 12 hours after administration of the first loading dose. In additionally preferred aspects, the loading dose is administered to a subject as two discrete loading doses, where each discrete loading dose is about 1500 mg, and where in the second loading dose is administered about 12 hours after administration of the first loading dose.

Maintenance Dose

The maintenance dose phase is the period of time following the loading dose phase where a particular minimum trough plasma concentration or plasma concentration of the FA is maintained in the subject. The skilled artisan will understand that the particular concentration of FA in the plasma, and the length of time needed to maintain the desired concentration, will depend on the condition that is being treated or prevented. While the methods of the invention may be practiced through the use of a single maintenance dose, the methods of the present invention will generally require that two or more maintenance doses be administered to a subject in order to maintain the desired minimum trough plasma concentration or plasma concentration of fusidic acid for a particular period of time.

In one embodiment of the invention, the maintenance dose is defined by the administration of fusidic acid to the subject in an amount sufficient to maintain a minimum trough plasma concentration of fusidic acid for a particular period of time. A minimum trough plasma concentration of not less than about 30, 35, 40, 45, 50, 55, 60, 65, 70, 75, 80, 85, 90, 95 or 100 ug/ml, or a value within this range, is maintained in the subject during the maintenance dose phase, preferably not less than about 70 ug/ml, more preferably not less than about 80 ug/ml. The minimum trough plasma concentration is maintained for a sufficient period of time to achieve the goal of the method being practiced (treatment or prevention) and will vary depending on the identity of the bacterial infection. However, it is considered that the minimum trough plasma concentration will need to be maintained at least about 12, 18, 24, 36, 48, 60, 72, 84, 96, 108, 120, 132, 144, 156, 168, 180, 192, 204, 216, 228, 240 or more hours, beginning from the time at which the last loading dose was administered to the subject. The first maintenance dose may be administered about 6, 7, 8, 9, 10, 11, 12, 13, 14, 15, 16, 17, 18 or more hours after the last loading dose.

In order to achieve particular minimum trough plasma concentrations, the specific amount of FA administered to a subject will depend on the characteristics of the subject, including age, weight, and general health. However, discrete maintenance doses will generally be about 200, 300, 400, 500, 600, 700, 800, 900, 1000, 1100, 1200 mg or more, or a value within this range. Preferably, each maintenance dose is between about 500 mg and 1000 mg. The amount of FA in each maintenance dose may be the same, or the doses may increase or decrease with time. The maintenance doses will be administered to the subject on a course of therapy determined by a physician, but in general the maintenance doses may be administered to the subject 1, 2, 3, 4, 5, 6 or more times per day, or a value within this range.

In an aspect, a minimum trough plasma concentration of not less than about 50 ug/ml is maintained for at least about 12, 18, 24, 36, 48, 60, 72, 84, 96, 108, 120, 132, 144, 156, 168, 180, 192, 204, 216, 228, 240 or more hours, or a value within this range, in particular at least about 24, 48 or 96 hours, after the last loading dose was administered to the subject.

The maintenance dose in the methods of the present invention may also be simply defined by the amount of fusidic acid in a discrete dose that is administered to a subject. Each discrete maintenance dose is individually about 200, 300, 400, 500, 600, 700, 800, 900, 1000, 1100, 1200 mg or more, or a value within this range. Preferably, each maintenance dose is between about 500 mg and 1000 mg. The discrete maintenance doses of FA may be administered 1, 2, 3, 4, 5, 6 or more times per day, or a value within this range. The first maintenance dose may be administered about 6, 7, 8, 9, 10, 11, 12, 13, 14, 15, 16, 17, 18 or more hours after the last loading dose. The maintenance dose phase is maintained for at least about 12, 18, 24, 36, 48, 60, 72, 84, 96, 108, 120, 132, 144, 156, 168, 180, 192, 204, 216, 228, 240 or more hours, or a value within this range, beginning from the time at which the last loading dose was administered to the subject. In a preferred aspect, at least three maintenance doses of 500 mg or 600 mg are administered to a subject during the maintenance dose phase, more preferably at least four doses, even more preferably at least five doses, wherein the maintenance doses are administered about 12 hours apart beginning about 12 hours after the last loading dose.

Combination of LD and MD

The skilled artisan will understand that different combinations of values for the three variables comprising the PK during the loading phase and the minimum trough plasma concentration during maintenance phase can be used, and that the exact values will depend on the condition being treated or prevented in the subject. However, in one example, the method of treating or preventing a bacterial infection in a subject comprises:

(a) administering at least one loading dose of fusidic acid, or a pharmaceutically acceptable salt thereof, to a subject in need of treatment or prevention, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 20 hours and a minimum trough plasma concentration of fusidic acid of not less than about 50 ug/ml, and (b) administering at least one maintenance dose of fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

In preferred aspects, the PK profile comprises (i) a $C_{max}$ of not less than about 80 ug/ml, (ii) a minimum trough plasma concentration of not less than about 60 ug/ml and (iii) a $T_{max}$ of no more than 20 hours, with the minimum trough plasma concentration being maintained at not less than about 70 ug/ml. In further preferred aspects, the PK profile comprises (i) a $C_{max}$ of not less than about 100 ug/ml, (ii) a minimum trough plasma concentration of not less than about 80 ug/ml and (iii) a $T_{max}$ of no more than 20 hours, with the minimum trough plasma concentration being maintained at not less than about 80 ug/ml.

The skilled artisan will also understand that different combinations of values for the minimum plasma concentration during the loading phase and the minimum trough plasma concentration during maintenance phase can be used, and that the exact values will depend on the condition being treated or prevented in the subject. However, in one example, the method of treating or preventing a bacterial infection in a subject comprises:

(a) administering at least one loading dose of fusidic acid, or a pharmaceutically acceptable salt thereof, to a subject in need of treatment or prevention in an amount sufficient to achieve a minimum plasma concentration of not less than about 50 ug/ml fusidic acid within 24 hours, and (b) administering at least one maintenance dose of fusidic acid, or a pharmaceutically acceptable salt thereof, to the subject of (a) in an amount sufficient to maintain a minimum plasma concentration of not less than about 50 ug/ml fusidic acid for at least about 24 hours after the administering of (a).

In a preferred aspect, a minimum plasma concentration of fusidic acid of not less than about 60 ug/ml is achieved in (a) and a minimum plasma concentration of fusidic acid of not less than about 60 ug/ml is maintained in (b). In a further preferred aspect, a minimum plasma concentration of fusidic acid of not less than about 80 ug/ml is achieved in (a) and a minimum plasma concentration of fusidic acid of not less than about 80 ug/ml is maintained in (b).

The skilled artisan will further understand that different combinations of values for loading phase doses and maintenance phase doses can be used, and that the exact values will depend on the condition being treated or prevented in the subject. However, in one example, the method of treating or preventing a bacterial infection in a subject comprises:

(a) administering a first and a second loading dose of fusidic acid, or a pharmaceutically acceptable salt thereof, to a subject in need of treatment or prevention, wherein each loading dose is independently between about 1000 mg and about 1850 mg, and wherein the second loading dose is administered about 12 hours after the first loading dose; and (b) administering two or more maintenance doses of fusidic acid, or a pharmaceutically acceptable salt thereof, to the subject of (a), wherein each maintenance dose is independently between about 500 mg and 1000 mg, wherein a first maintenance dose is administered about 12 hours after administration of the second loading dose, and wherein subsequent maintenance doses are administered about 12 hours apart.

In a preferred aspect, at least three, four, five or six maintenance doses are administered to the subject. In a further preferred aspect, each loading dose is independently at least about 1500 mg and each maintenance dose is independently at least about 600 mg.

Preventing Development of Resistant Strains of Bacteria

The present invention is also directed to methods for reducing development of antibiotic-resistant strains of bacteria in a subject undergoing antibiotic therapy. These methods are also based on the novel dosing regimens disclosed herein. As in the methods of treating or preventing bacterial infections described herein, the methods for reducing development of antibiotic-resistant strains of bacteria are based on the novel dosing regimens comprising a loading dose phase and a maintenance dose phase. All aspects of the loading dose phase and the maintenance dose phase described above for the methods of treating or preventing bacterial infections are the same for the loading dose phase and the maintenance dose phase of the methods for reducing development of antibiotic-resistant strains of bacteria and are specifically incorporated herein.

The skilled artisan will understand that different combinations of values for the three variables comprising the PK during the loading phase and the minimum trough plasma concentration during maintenance phase can be used, and that the exact values will depend on the bacterial infection for which a subject is undergoing treatment. However, in one example, the method for reducing development of antibiotic-resistant strains of bacteria in a subject having a bacterial infection comprises:

(a) administering at least one loading dose of fusidic acid, or a pharmaceutically acceptable salt thereof, to a subject having a bacterial infection, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 24 hours and a minimum trough plasma concentration of fusidic acid of not less than about 50 ug/ml, and (b) administering at least one maintenance dose of fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

In a preferred aspect, the $C_{max}$ is not less than about 80 ug/ml, the minimum trough plasma concentration of (a) is not less than about 60 ug/ml, and the minimum trough plasma concentration of (b) is not less than about 70 ug/ml. In a further preferred aspect, the $C_{max}$ is not less than about 100 ug/ml, the minimum trough plasma concentration of (a) is not less than about 80 ug/ml and the minimum trough plasma concentration of (b) is not less than about 80 ug/ml.

In each of the embodiments of the present invention, the following common aspects and preferred common aspects are encompassed within the scope of the invention.

Fusidic Acid (FA) has the following structure.

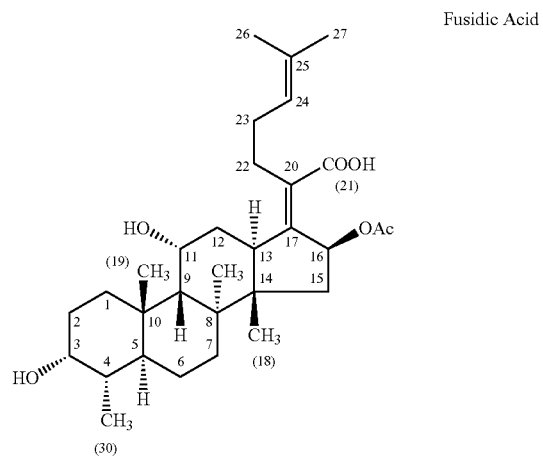

Fusidic Acid

The skilled artisan will understand that for the sake of brevity alone, all references herein to "fusidic acid" or "FA", unless otherwise stated, also refers to the hemihydrate form of the compound, as well as pharmaceutically acceptable salts, other hydrates, solvates, or mixtures thereof.

The term "pharmaceutically acceptable salt" refers to non-toxic base addition salts derived from inorganic and organic bases. Base addition salts include those derived from inorganic bases, such as ammonium or alkali or alkaline earth metal hydroxides, carbonates, bicarbonates, and the like, as well as alkylamine and organic amino salts, such as an ethanolamine salt. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. In preferred embodiments, sodium fusidate is a pharmaceutically acceptable salt that is used in the methods of the present invention. Sodium fusidate, also termed CEM-102 herein, has the following structure.

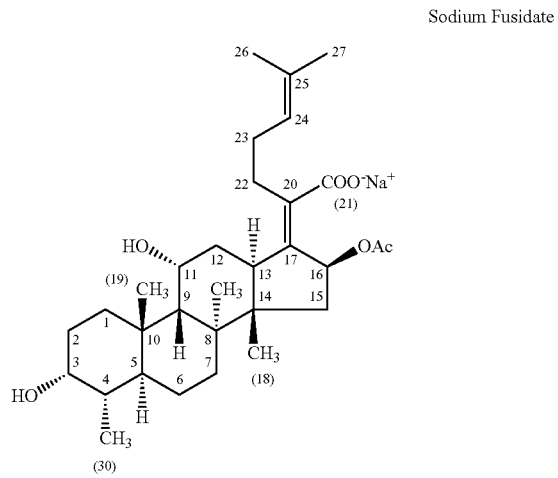

Sodium Fusidate

It should be recognized that the particular counter-ion forming a part of any salt of this invention is not of a critical nature, so long as the salt as a whole is pharmacologically acceptable and as long as the counter-ion does not contribute undesired qualities to the salt as a whole.

In each of the embodiments of the present invention, the subject being subjected to treatment or prevention is a human, non-human primate, bird, horse, cow, goat, sheep, a companion animal, such as a dog, cat or rodent, or other mammal. The subject may have a bacterial infection, such as where the present invention is directed to methods for treating a bacterial infection in a subject. The subject may also be at risk for developing a bacterial infection, such as where the present invention is directed to methods for preventing a bacterial infection in a subject. Examples of subjects at risk for developing bacterial infections include patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly, children, people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., hospitals and medial clinics, prisons, military, nursing homes), people having cystic fibrosis, people that have immunological deficiencies that might enhance their susceptibility to bacterial infection, people entering an emergency room, such as those with wounds or cellulitis, and patients leaving a hospital on step-down therapy after having been on intravenous therapy In each of the embodiments of the present invention, the bacterial infection being treated or prevented is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. In particular aspects, the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*. In particular aspects, the bacterial infection is an infection caused by *Enterococcus faecalis* or *Enterococcus faecium.*

In each of the embodiments of the present invention, the bacterial infection may also be defined based on the type of infection that it causes. For example, each of the embodiments of the present invention may be used to treat or prevent an infection selected from the group consisting of a skin and soft tissue infection, a bone infection, a joint infection, pneumonia, a wound infection, a burn infection, an infection of the blood, and an infection associated with cystic fibrosis.

In each of the embodiments of the present invention, the fusidic acid may be administered to a subject in conjunction with a second therapeutic agent, such as a second antibiotic. The second therapeutic agent may be administered before, concurrent with or after administration of the fusidic acid, whether in the same formulation or in a separate formulation. Suitable second therapeutic agents include rifampin, rifamycin, a sulfonamide, a beta-lactam, a tetracycline, a chloramphenicol, an aminoglycoside, a macrolide, a streptogramin, a quinolone, a fluoroquinolone, an oxazolidinone and a lipopeptide. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, and daptomycin derived antibacterial agents are preferred. In a preferred aspect of the embodiments, rifampin is administered concurrently with the fusidic acid.

In each of the embodiments of the present invention, the subject does not experience an adverse level of nausea over the entire course of treatment or prevention. As used herein, an adverse level of nausea is considered to be a level of nausea severe enough that at least 15% of subjects in a population of subjects being treated with fusidic acid discontinue treatment.

The pharmaceutical compositions of the present invention comprise fusidic acid, a hemihydrate form thereof, or pharmaceutically acceptable salts, other hydrates, solvates, or mixtures thereof, and one or more of a carrier, diluent and excipient. The terms specifically exclude cell culture medium. Suitable diluents (for both dry and liquid pharmaceutical formulations) are well known to those skilled in the art and include saline, buffered saline, dextrose (e.g., 5% dextrose in water), water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717).

Carriers are compounds and substances that improve and/or prolong the delivery of an active ingredient to a subject in the context of a pharmaceutical formulation. Carrier may serve to prolong the in vivo activity of a drug or slow the release of the drug in a subject, using controlled-release technologies. Carriers may also decrease drug metabolism in a subject and/or reduce the toxicity of the drug. Carrier can also be used to target the delivery of the drug to particular cells or tissues in a subject. Common carriers (both hydrophilic and hydrophobic carriers) include fat emulsions, lipids, PEGylated phospholids, liposomes and liposheres, microspheres (including those made of biodegradable polymers or albumin), polymer matrices, biocompatible polymers, protein-DNA complexes, protein conjugates, erythrocytes, vesicles and particles.

Excipients included in a pharmaceutical composition have different purposes depending, for example on the nature of the drug, and the mode of administration. Examples of generally used excipients include, without limitation: stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

In particular, the pharmaceutical compositions may contain common carriers and excipients, such as microcrystalline cellulose, crospovidone, hypromellose, lactose monohydrate, magnesium stearate, silica, all-rac-α-tocopherol, talc and titanium dioxide.

Pharmaceutically acceptable excipients also include tonicity agents that make the composition compatible with blood. Tonicity agents are particularly desirable in injectable formulations.

The particular carrier, diluent or excipient used will depend upon the means and purpose for which the active ingredient is being applied.

The pharmaceutical compositions of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vasoconstrictors for prolongation and agents that increase tissue permeability), and combinations thereof Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form can be a ready-to-use solution of the active ingredient in a suitable carrier in sterile, hermetically sealed ampoules or in sterile pre-loaded syringes. The suitable carrier optionally comprises any of the above-mentioned excipients.

Alternatively, the unit dosage of the pharmaceutical composition can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose in water or Ringer's™ solution.

In a preferred intravenous (IV) formulation, fusidic acid is dissolved in a buffered solution (pH 7.4-7.6) containing disodium hydrogen phosphate, citric acid, disodium edetate and water for injections. The buffered solution is then added to a suitable infusion, such as a sodium chloride intravenous infusion, a dextrose intravenous infusion, a compound sodium lactate intravenous infusion ("Ringer-lactate solution"), a sodium lactate intravenous infusion, sodium chloride and dextrose intravenous infusion, or potassium chloride and dextrose intravenous infusion. Suitable amounts of fusidic acid to be dissolved in the buffered solution range from about 10 to about 4000 mg, with preferred amounts including about 250, 300, 350, 400, 450, 500, 550, 600, 650, 700, 750, 800, 850, 900, 950, or 1000 mg of fusidic acid, or a value within this range. Preferably, the final concentration of fusidic acid in the intravenous infusion is about 1, 2, 3, 4, 5, 6, 7, 8, 9, 10, 15, 20, 25, 30, 35 or 40 mg/ml or more. Suitable periods of time over which the fusidic acid-containing intravenous infusion may be administered include 15, 30, 45 or 60 minutes, or 1, 1.5, 2, 2.5, 3, 3.5, 4, 4.5 or 5 or more hours.

In intramuscular preparations, a sterile formulation of the pharmaceutical composition of the present invention can be dissolved and administered in a pharmaceutical diluent such as Water-for-Injection (WFI), physiological saline or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate. Suitable amounts of fusidic acid to be administered in a formulation for injection range from about 10 to about 4000 mg, with preferred amounts including about 10, 25, 50, 100, 150, 200, 250, 300, 350, 400, 450, 500, 550, 600, 650, 700, 750, 800, 850, 900, 950, or 1000 mg of fusidic acid, or a value within this range.

For oral use, the oral pharmaceutical composition may be made in the form of a unit dosage containing a therapeutically-effective amount of the pharmaceutical composition. Solid formulations such as tablets and capsules are particularly useful. Sustained released or enterically coated preparations may also be devised. For pediatric and geriatric applications, suspension, syrups, slow release and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to fusidic acid, inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavoring (e.g. peppermint, oil of wintergreen, fruit flavoring, cherry, grape, bubblegum, and the like), and coloring agents. The tablets and capsules may also include coating excipients such as glyceryl monostearate or glyceryl distearate, to delay absorption in the gastrointestinal tract.

In a particular oral formulation, the pharmaceutical compositions of the present invention may be in the form of a tablet containing microcrystalline cellulose, crospovidone, hypromellose, lactose monohydrate, magnesium stearate, silica, all-rac-α-tocopherol, talc and titanium dioxide, and optionally one or more other inactive ingredients. Suitable amounts of fusidic acid in a tablet may range from about 10 to about 4000 mg, with preferred amounts including about 250, 300, 350, 400, 450, 500, 550, 600, 650, 700, 750, 800, 850, 900, 950, or 1000 mg of fusidic acid per tablet, or a value within this range.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid. In a particular oral formulation, the pharmaceutical composition comprises fusidic acid and the following inactive ingredients: acesulfame potassium, flavor, citric acid, disodium phosphate dihydrate, hydroxyethylcellulose, glucose liquid, methylcellulose, sodium benzoate, sorbitol, and purified water. Suitable amounts of fusidic acid in an oral formulation may range from about 10 to about 4000 mg, with preferred amounts including about 250, 300, 350, 400, 450, 500, 550, 600, 650, 700, 750, 800, 850, 900, 950, or 1000 mg of fusidic acid in the oral formulation, or a value within this range.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride. In particular embodiment, a cream may be prepared comprising fusidic acid and the following inactive ingredients: steareth-21, cetostearyl alcohol, white soft paraffin, liquid paraffin, hypromellose, citric acid monohydrate, methyl parahydroxybenzoate, propyl parahydroxybenzoate, potassium sorbate, and purified water, or the following inactive ingredients: butylated hydroxyanisole, cetanol, glycerol, liquid paraffin, potassium sorbate, Tween 60, white soft paraffin, and purified water. In another particular formulation, an eye drop may be prepared comprising fusidic acid and the following inactive ingredients: benzalkonium chloride, disodium edetate, mannitol, carbomer, sodium hydroxide, and water. Suitable amounts of fusidic acid in an eye drop formulation may range from about 1 to about 100 mg, with preferred amounts including about 5, 10, 15, 20, 25, 30, 35, 40, 45, 50, 55, 60, 65, 70, 75, 80, 85, 90, 95, or 100 mg of fusidic acid in the formulation, or a value within this range.

For pulmonary administration, the pharmaceutical compositions of present invention can be prepared in suitable forms for inhalation (an inhalable formulation; for nasal or buccal inhalation). The compounds may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of this invention in suitable propellants, such as fluorocarbons or hydrocarbons.

As used herein, the terms "dose", "dosage", "unit dose", "unit dosage", "effective dose" and related terms refer to physically discrete units that contain a predetermined quantity of active ingredient calculated to produce a desired therapeutic effect. These terms are synonymous with the therapeutically effective amounts and amounts sufficient to achieve the stated goals of the methods disclosed herein. The skilled artisan will understand that the term "maintenance dose" can refer to single discrete dose, as well as more than one discrete dose. The maintenance dose is the total amount of FA administered during the maintenance dose phase. Similarly, the term "loading dose" can refer to single discrete dose, as well as more than one discrete dose. The loading dose is the total amount of FA administered during the loading dose phase.

As used herein, the terms "treating" and "treatment" have their ordinary and customary meanings, and include one or more of, ameliorating a symptom of a bacterial infection in a subject, blocking or ameliorating a recurrence of a symptom of a bacterial infection in a subject, decreasing in severity and/or frequency a symptom of a bacterial infection in a subject, stasis, decreasing, or inhibiting growth of bacteria in a subject, killing bacteria in a subject, inhibiting bacterial sporulation, inhibiting activation of a bacterial spore in a subject, inhibiting germination of a bacterial spore in a subject, and inhibiting outgrowth of a bacterial spore in a subject. Treatment means ameliorating, blocking, reducing, decreasing or inhibiting by about 1% to about 100% versus a subject to which a pharmaceutical composition has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition has not been administered.

As used herein, the terms "preventing" and "prevention" have their ordinary and customary meanings, and include one or more of preventing bacterial colonization in a subject, preventing an increase in the growth of a bacterial population in a subject, preventing activation, germination or outgrowth of bacterial spores in a subject, preventing bacterial sporulation in a subject, preventing development of a disease caused by a bacterial infection in a subject, and preventing symptoms of a disease caused by a bacterial infection in a subject. As used herein, the prevention lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

EXAMPLES

Example 1

Study of the Spectrum of CEM-102 (Fusidic Acid) Against Contemporary Wildtype (WT) Bacterial Species Including Mutational Resistance (R) Analysis, and Synergy Testing Methods: A collection of 114 WT isolates (>80 species) was used to define the contemporary limits of CEM-102 (fusidic acid; FA) spectrum against Gram-positive (GP) and -negative (GN) species. CLSI broth microdilution (BMD) and anaerobic agar dilution (AD) methods were performed. Modifications of standard test methods included adding 10% human serum, adjusting the medium pH to 5, 6, and 8, and synergy was assessed by the checkerboard method. Mutational rates to R were determined at 4×, 8× and 16×MIC.

Results: Against GP, FA MIC values ranged from 0.06-32 µg/ml with greatest potency against *S. aureus, Corynebacterium* spp. and *M. luteus* (MIC results 0.25, ≦0.12 and ≦0.5 µg/ml, respectively). Enterococci and streptococci were less susceptible (S; MIC ranges of 2-8 and 16-32 µg/ml, respectively).

When tested against 217 *S. aureus* Canadian isolates, the $MIC_{50}$ for CEM-102 was 0.12 µg/mL and the $MIC_{90}$ was 0.25 µg/mL, which is only slightly higher than strains in the US ($MIC_{90}$ 0.12 µg/mL). The MIC population distribution study showed that only 6.5% of the Canadian *S. aureus* isolates had MICs of ≧2.0 µg/mL and would be classified as resistant. By comparison, ciprofloxacin, clindamycin, and erythromycin resistance rates were 41.5, 30.9, and 52.1% respectively). This is based upon established breakpoints of greater than or equal to 2 ug/ml (more strains are expected to be classified as susceptible in view of the dosing regimes disclosed in the present application due to the much higher blood levels of FA; many resistant strains, with MICs of 4-32 ug/ml, are expected to be susceptible under the new dosing regimens).

FA activity against GN species was limited (all MIC values ≧2 µg/ml) except for *E. brevis, M. catarrhalis* and *N. meningitidis* (MICs, 0.12-0.5 µg/ml).

A 4-fold increase in FA MIC results was observed when 10% serum was added.

Decreasing medium pH to 5.0-6.0 negated the protein binding effects.

Among the 8 combinations of drugs tested, gentamicin (GEN) and rifampin (RIF) showed the greatest enhanced activity combined with FA (No antagonism; Table 1). Single-step mutational rates ranged from $1.2 \times 10^{-6}$ for 4×MIC to $9.8 \times 10^{-8}$ for 16×MIC.

TABLE 1

| FA/co-drug | Synergy | | | | | |
|---|---|---|---|---|---|---|
| | Complete | Partial | Additive | Indifferent | Antagonism | Indeterminate |
| Rifampin | 0 | 5 | 1 | 0 | 0 | 0 |
| Levofloxacin | 0 | 0 | 0 | 4 | 0 | 2 |
| Gentamicin | 1 | 1 | 3 | 1 | 0 | 0 |
| Oxacillin | 0 | 1 | 1 | 3 | 0 | 1 |
| Vancomycin | 0 | 0 | 2 | 4 | 0 | 0 |
| All agents tested | 1 | 7 | 9 | 24 | 0 | 7 |

Conclusions: FA demonstrated potent GP activity, especially against the staphylococci. A more limited activity was observed against GN species isolates. Added serum proteins adversely influenced MIC values; however lower media pH like seen at infection sites decreased negative protein binding effects. FA in vitro activity was most improved when combined with RIF.

Example 2

Antimicrobial Activity of CEM-102 (Fusidic Acid) Against Canadian Isolates of Staphylococci and Streptococci.

Methods: To determine a contemporary susceptibility (S) spectrum pattern, 153 GP isolates (123 *S. aureus*, 15 coagulase-negative staphylococci [CoNS] and 15 *S. pyogenes* [SPYO]) were collected from 5 Canadian medical centers between 2001 and 2006. Reference broth microdilution (BMD) S testing was performed by CLSI M07-A8, 2009 methods for FA and 13 comparator antimicrobials.

Results: FA MIC results for *S. aureus* had $MIC_{50}$ and $MIC_{90}$ values of 0.12 µg/mL for the 2001-2002 and 2003-2004 time periods, however, for 2005-2006 the $MIC_{90}$ increased to ≧2 µg/ml (Table 2). Applying an international breakpoint from literature reviews at ≦0.5 µg/ml (S) and ≧2 µg/ml (R), the *S. aureus* isolates showed a small increase in the R rate over time (5.0-12.2%), now confirmed by 2007-2008 results. The overall *S. aureus* population had a $MIC_{90}$ of 0.25 µg/ml and R rate of 8.1%. Some comparator agents showed higher R rates that remained stable over the period tested with highest R noted for erythromycin (ERY, 52.0%), ciprofloxacin (43.9%), and clindamycin (CLI, 28.5%). CoNS isolates had FA $MIC_{50}$ and $MIC_{90}$ values at 0.12 and 16

μg/ml, respectively. SPYO isolates were only moderately S to FA with all values at 4 or 8 μg/ml. Among the comparator agents, ERY had an R rate of 20.0% and CLI at 13.3% for SPYO.

TABLE 2

| S. aureus (years tested) | No. inhibited at MIC (μg/mL) of: | | | | | | | % at ≤0.5[a] |
|---|---|---|---|---|---|---|---|---|
| | ≤0.03 | 0.06 | 0.12 | 0.25 | 0.5 | 1 | ≥2 | |
| 2001-2002 | — | 8 | 29 | 1 | — | — | 2 | 95.0 |
| 2003-2004 | — | 6 | 33 | — | — | — | 3 | 92.9 |
| 2005-2006 | — | 2 | 32 | 2 | — | — | 5 | 87.8 |

[a]6.0% R for 2007-2008

Conclusions: FA demonstrated potent activity against Canadian staphylococci isolates with a low overall R rate (8.1%) among *S. aureus*. CoNS isolates had a greater R rate than *S. aureus*. FA had a narrow range of MIC results (4-8 μg/ml) and was less active against SPYO.

Example 3

In Vitro Activity of CEM-102 (Fusidic Acid) Against Resistant Strains of *Staphylococcus aureus*

The activity of CEM-102 (fusidic acid) against a variety of resistant strains of *Staphylococcus aureus* was investigated.

Methods: The in vitro activity of CEM-102 was compared with that of telithromycin, azithromycin, erythromycin, levofloxacin, linezolid, and doxycycline against a total of 145 resistant *S. aureus* by agar dilution procedures (CLSI, M7-A7, M100-S18). The tested strains included *S. aureus* MRSA (Mec A genotype; 100 isolates), macrolide-resistant (ermA, B, C genotype or MLSb-resistant; 25), and ciprofloxacin-resistant (gyrA and parC genotype; 20).

Results: Against *S. aureus* MRSA (MecA), CEM-102 ($MIC_{90}$ 0.25 mg/L) and telithromycin ($MIC_{90}$ 0.06 mg/L) were more active than doxycycline ($MIC_{90}$ 1 mg/L), linezolid ($MIC_{90}$ 2 mg/L), levofloxacin ($MIC_{90}$ 16 mg/L), azithromycin ($MIC_{90}$>32 mg/L) and erythromycin ($MIC_{90}$>32 mg/L). CEM-102 ($MIC_{90}$ 0.25 mg/L) was significantly superior to linezolid ($MIC_{90}$ 2 mg/L), levofloxacin ($MIC_{90}$ 4 mg/L), telithromycin ($MIC_{90}$ 4 mg/L), azithromycin ($MIC_{90}$>32 mg/L), and erythromycin ($MIC_{90}$>32 mg/L) against macrolide-resistant *S. aureus* (ermA, B, C genotype or MLSb-resistant). Against ciprofloxacin-resistant (gyrA and parC genotype) *S. aureus*, erythromycin ($MIC_{90}$>32 mg/L), levofloxacin ($MIC_{90}$>32 mg/L), azithromycin ($MIC_{90}$ 16 mg/L), linezolid ($MIC_{90}$ 2 mg/L), and doxycycline ($MIC_{90}$ 1 mg/L) were less active than CEM-102 ($MIC_{90}$ 0.25 mg/L) and telithromycin ($MIC_{90}$ 0.06 mg/L).

Conclusions: These data confirm the activity of CEM-102 against resistant *S. aureus* and show the promise of this unique antibiotic that has no cross resistance with other classes of antibiotics.

Example 4

Single Oral Dose Bioavailability Study of CEM-102 (Sodium Fusidate)

The primary objective of the study was to evaluate the relative bioavailability of single oral doses of CEM-102 (sodium fusidate) 500 mg (2×250 mg) tablets and Fucidin® (sodium fusidate) 500 mg (2×250 mg) tablets in healthy subjects in a fed or fasted state.

This was a single-center, Phase 1, double-blind, randomized, 3 period, fed/fasted crossover bioequivalence study designed to evaluate the relative bioavailability and safety and tolerability of a single oral dose of CEM-102 500 mg compared to Fucidin® 500 mg in healthy subjects.

Subjects were randomized in equal numbers to the 4 treatment sequences (Table 3).

TABLE 3

| Treatment Sequence | Subjects Randomized | Study Period 1 | Study Period 2 | Study Period 3 |
|---|---|---|---|---|
| 1 | 7 | Fucidin ® 500 mg (2 × 250 mg) Fasting | CEM-102 500 mg (2 × 250 mg) Fasting | Fucidin ® 500 mg (2 × 250 mg) Fed |
| 2 | 7 | Fucidin ® 500 mg (2 × 250 mg) Fasting | CEM-102 500 mg (2 × 250 mg) Fasting | CEM-102 500 mg (2 × 250 mg) Fed |
| 3 | 7 | CEM-102 500 mg (2 × 250 mg) Fasting | Fucidin ® 500 mg (2 × 250 mg) Fasting | Fucidin ® 500 mg (2 × 250 mg) Fed |
| 4 | 7 | CEM-102 500 mg (2 × 250 mg) Fasting | Fucidin ® 500 mg (2 × 250 mg) Fasting | CEM-102 500 mg (2 × 250 mg) Fed |

Study Period 1, 2, and 3 (Days 1, 15, and 29): One dose of study drug 500 mg (2×250 mg) of CEM-102 or Fucidin® was given at 8:00 AM (~30 minutes). On Day 1 of Study Periods 1 and 2 (Days 1 and 15), subjects fasted overnight for at least 10 hours prior to dosing. On Day 1 of Study Period 3 (Day 29), subjects were given a high fat caloric meal which was to be entirely consumed within 30 minutes prior to study drug administration.

Figure 2:
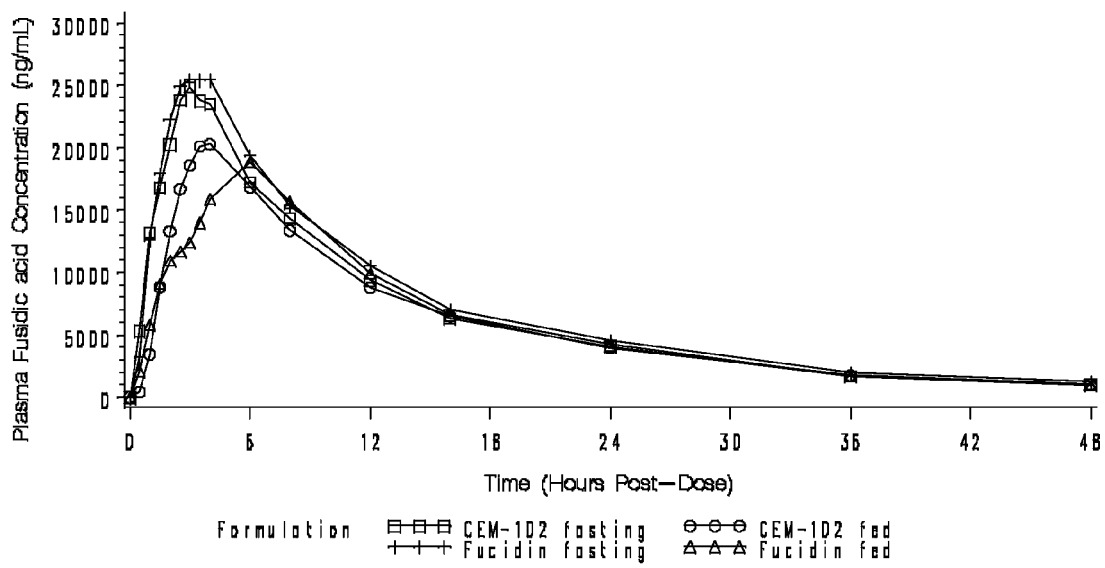
FIG. 2—Mean plasma concentrations of fusidic acid after a single dose of sodium fusidate (linear plot).

Blood samples for assay of plasma concentrations were collected on Days 1, 15 and 29 at pre-dose and 0.5, 1, 1.5, 2, 2.5, 3, 3.5, 4, 6, 8, 12, 16, 24, 36, and 48 hours after the dose. Plasma concentrations were assayed at MicroConstants, Inc. in San Diego, Calif. using a validated liquid chromatography with dual tandem mass spectrometry (LC/MS/MS) method with a lower limit of quantitation (LLOQ) of 20.0 ng/mL Mean plasma concentrations of fusidic acid are depicted in FIGS. 1 and 2 on semi-log and linear scales. The median (minimum-maximum) $t_{max}$ values for fusidic acid for the CEM-102 and Fucidin® products under fasting conditions were 3.00 hours (1.00 to 4.00 hours) and 2.52 hours (1.00 to 6.00 hours), respectively.

Descriptive statistics of pharmacokinetic results for fusidic acid in plasma are presented in Table 4.

TABLE 4

Descriptive Statistics for the Assessment of Food-effect and Fed Pharmacokinetics

|  | Parameter | CEM-102 Fed (C) | CEM-102 Fasting (A) | Fucidin® Fed (D) |
|---|---|---|---|---|
| Geometric Mean (CV %) | $AUC_{0-t}$ (ng · h/mL) | 268561 (31.5) | 300352 (30.9) | 264713 (40.5) |
|  | $AUC_{inf}$ (ng · h/mL) | 285056 (32.7) | 318391 (32.0) | 280680 (40.5) |
|  | $C_{max}$ (ng/mL) | 21175 (25.2) | 27413 (23.8) | 21541 (34.0) |
| Arithmetic Mean ± SD | $t_{1/2}$ (h) | 11.5 ± 2.75 | 11.8 ± 2.20 | 11.5 ± 2.62 |
| Median (Min-Max) | $t_{max}$ (h) | 3.50 (1.50-6.00) | 3.00 (1.00-4.00) | 4.00 (1.00-8.25) |

Food appeared to decrease the $C_{max}$ of CEM-102 by approximately 23%. However, the total exposure (AUC), the time to peak plasma concentrations and the half-life were comparable when the CEM-102 500 mg dose was administered under fed and fasting conditions (approximately 285 vs. 318 μg·h/mL, 3.50 vs. 3.00 hours and 11.5 vs. 11.8 hours, respectively)

Example 5

Multi-dose Bioavailability Study Using FA at 500 mg TID

The pharmacokinetics of multiple oral doses of CEM-102 (sodium fusidate) 500 mg tablets in healthy subjects was evaluated. Subjects were randomized in a 3:1 ratio and received either CEM-102 500 mg (2×250 mg; n=18) or placebo tablets TID (n=6) for 4.5 days for a total of 13 doses.

Blood samples for assay of plasma concentrations of CEM-102 and placebo were collected pre-dose on Day 1 and at 24, 48, 72, and 96 hours. Samples were also collected at the following times after the morning dose on Day 5: 0.5, 1, 1.5, 2, 2.5, 3, 3.5, 4, 6, 8, 12, 16, 24, 36, and 48 hours.

Plasma concentrations of CEM-102 were assayed at MicroConstants, Inc. in San Diego, Calif., USA using a validated LC/MS/MS method with a lower limit of quantitation (LLOQ) of 20.0 ng/mL.

Figure 3:
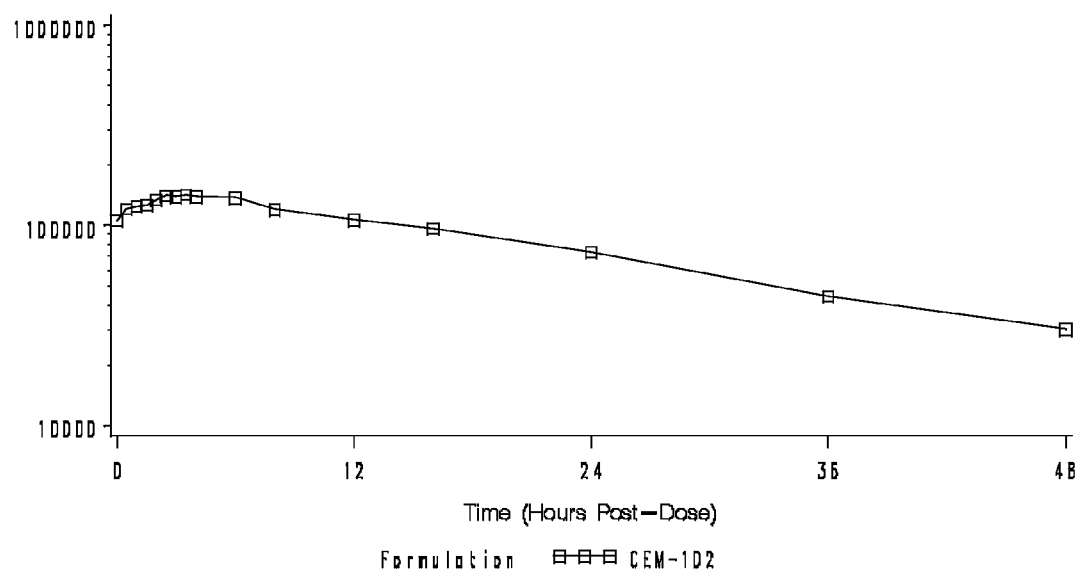
FIG. 3—Mean plasma concentrations of CEM-102 (Sodium fusidate) after 13 doses—semi-log plot.
Figure 4:
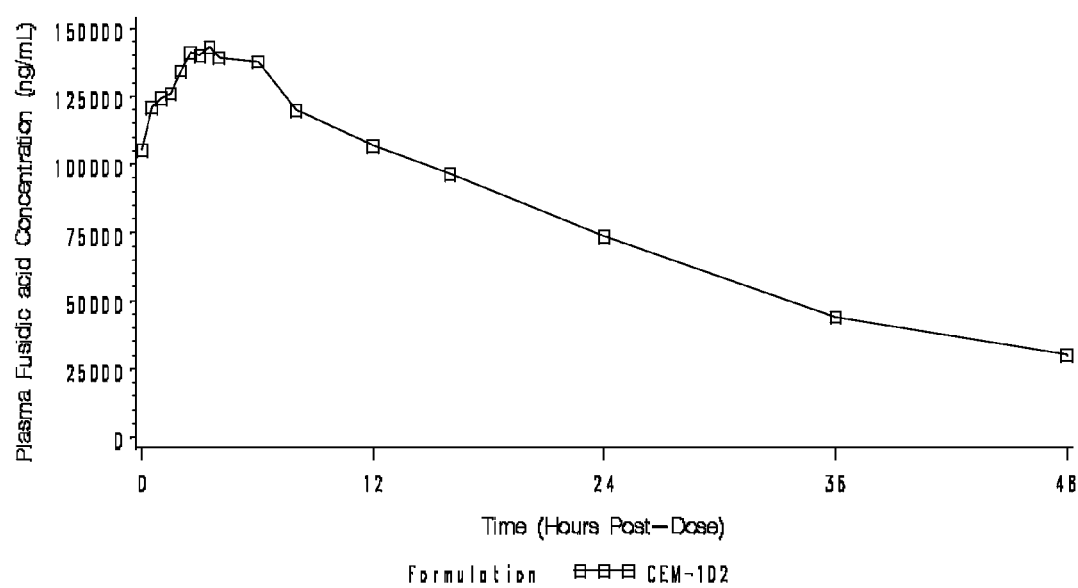
FIG. 4—Mean plasma concentrations of CEM-102 (Sodium fusidate) after 13 doses—linear plot.

Mean plasma concentrations of CEM-102 on Day 5 (13 doses) are depicted on semi-log (FIG. 3) and linear scales (FIG. 4).

Descriptive statistics of pharmacokinetic results for CEM-102 in plasma are presented in Table 5.

TABLE 5

|  | Parameter | CEM-102 in Plasma (Day 5) |
|---|---|---|
| Geometric Mean (CV %) | AUC0-tss (ng · h/mL) | 3562344 (34.7) |
|  | AUC0-τss (ng · h/mL) | 1030827 (26.3) |
|  | Cmaxss (ng/mL) | 145680 (25.3) |
|  | Cmin (ng/mL) | 106600 (25.5) |
| Arithmetic Mean ± SD | t½ss (h) | 18.7 ± 5.30 |
| Median (Min-Max) | tmaxss (h) | 3.00 (0.50-6.00) |

On Day 5, the PK profile of CEM-102 in plasma following repeated oral doses of 500 mg TID was well characterized. Mean plasma concentrations of CEM-102 remained above the LLOQ (20.0 ng/mL) throughout the sampling schedule. Mean CEM-102 concentrations rose rapidly and peaked at approximately 3 hours (range 0.5-6 hours) post-dose and then declined slowly with an apparent half-life of approximately 19 hours. Maximum plasma concentrations ranged between 87.6 and 245 ug/mL. Trough levels rose steadily from Days 1 through 5 attaining 105 ug/mL prior to dosing on Day 5 and 120 ug/mL at 8 hours post-dose. This continuing rise in mean trough concentrations following the last dose may indicate that steady-state was not yet reached by Day 5.

The pharmacokinetic profile of CEM-102 in plasma following multiple oral doses of 500 mg administered TID for 13 doses over 4.5 consecutive days was well characterized. However, the continuing rise in mean trough concentrations following the last dose may indicate that steady-state was not yet reached by Day 5.

The results of this study supported the published reports that a steady state high level of FA is not reached until after the 4th day using the standard dosing regimen of 500 mg TID.

Example 6

Dose Escalation Study Using Single- and Multi-Dose FA

The pharmacokinetics (PK), safety, and tolerability of single and multiple doses of CEM-102 (sodium fusidate) were evaluated in a single-center, Phase 1, double-blind, randomized, placebo-controlled, dose-escalating study in 32 healthy adult subjects enrolled in 4 dosage groups (550, 1100, 1650, and 2200 mg). In each cohort, six subjects were to receive CEM-102 and two were to receive placebo in a single dose (Period 1) and then multiple doses BID for a total of 11 doses over 5.5 days (Period 2). The two dosing periods were separated by a seven-day washout period between the single dose in Period 1 and the first dose in Period 2.

Dosing proceeded as planned for Cohorts 1 to 3; however, Cohort 4 received only the single dose of 2200 mg (Period 1), because dose-limiting gastrointestinal intolerance was observed after multiple doses of 1650 mg BID in Cohort 3. Period 2 for Cohort 4 evaluated an initial loading dose regimen, and a second loading dose regimen was evaluated in an additional cohort (Cohort 5) per a protocol amendment.

CEM-102 was considered safe and generally well tolerated. No serious or life-threatening adverse events (AEs) occurred. Seventy-four AEs were reported in 19 of the 32 study subjects, all of which were mild or moderate in severity. Of the 70 treatment-emergent AEs reported all except 7 were in Period 2, in which subjects received multiple daily doses over 5.5 days. Most of the AEs were considered possibly related to study drug.

Single doses of CEM-102 up to 2200 mg were well tolerated. The only AEs reported in the 550 mg and 1100 mg cohorts were in subjects on placebo and no AEs were reported in the 1650 mg cohort. As described in product information documents from countries in which sodium fusidate is approved and from published reports, gastrointestinal AEs are the most commonly reported AEs associated with administration of oral sodium fusidate. In the present study, no gastrointestinal AEs were reported in the 550, 1100, or 1650 mg cohorts (Table 6). Nausea and vomiting occurred in 1 subject after the single dose of 2200 mg and nausea alone occurred in 2 others; therefore, gastrointestinal intolerance appeared to be dose-related with a threshold between 1650 and 2200 mg. There were no clinically significant changes in physical examinations, vital signs, electrocardiograms (ECGs), or laboratory parameters after single doses of CEM-102.

As with single doses, the most common AE after multiple doses of CEM-102 was nausea, reported in 9 subjects (550 mg, 2 subjects; 1100 mg, 2 subjects; 1650 mg, 5 subjects) (Table 7). Nausea occurred most frequently after 3 to 5 days of dosing with 1650 mg BID. No pharmacologic treatment was required for most of the AEs.

Four of the subjects at the 1650 mg multiple dose level also experienced vomiting (Grade 1 in 3 subjects and Grade 2 in 1 subject). Although the vomiting was considered mild in 3 of the 4 subjects, the decision was made to limit evaluation of multiple doses to the 1650 mg dose level. Consequently, escalation to the 2200 mg dose in Cohort 4 involved only Period 1 with a single dose of study drug.

TABLE 6

CEM-102 Single-Dose Treatment-emergent Adverse Events

| Cohort/ Treatment | Subject # | Gender Age (Y) | Day | Adverse Event | Frequency | Severity Grade | Relationship | Treatment | Outcome |
|---|---|---|---|---|---|---|---|---|---|
| 550 mg | 12 | M/48 | 1 | BP elevation | x1 | 1 | Possibly | None | Recovered |
| 1100 mg | 37 | F/46 | 3 | Headache | Constant | 1 | Possibly | None | Recovered |
| 1650 mg | — | — |   | None | — | — | — | — | — |
| 2200 mg | 67 | F/54 | 2 | Abdomen distention | Constant | 1 | Unlikely | None | Recovered |
|   | 80 | F/21 | 1 | Nausea | x1 | 1 | Probably | None | Recovered |
|   |   |   | 1 | Vomiting | x1 | 1 | Probably | None | Recovered |
|   | 81 | F/54 | 1 | Nausea | x1 | 1 | Probably | None | Recovered |
|   | 85 | M/51 | 1 | Nausea | x1 | 1 | Probably | None | Recovered |

TABLE 7

CEM-102 Multiple-Dose Treatment-Emergent Adverse Events (Blinded)

| Cohort/ Treatment | Subject # | Gender Age (Y) | Day | Adverse Event | Frequency | Severity Grade | Relationship | Treatment | Outcome |
|---|---|---|---|---|---|---|---|---|---|
| 550 mg | 01 | F/48 | 2 | Hoarseness | Constant | 1 | Unrelated | None | Recovered |
|   |   |   | 3 | Sore throat | Constant | 1 | Unrelated | None | Recovered |
|   | 02 | F/31 | 1 | Nausea | x1 | 1 | Possibly | None | Recovered |
|   |   |   | 2 | Nausea | x1 | 1 | Possibly | None | Recovered |
|   |   |   | 3 | Nausea | x1 | 1 | Possibly | None | Recovered |
|   |   |   | 6 | Nausea | x1 | 1 | Possibly | None | Recovered |
|   |   |   | 7 | Epigastric pain | x1 | 1 | Possibly | None | Recovered |
|   | 17 | M/21 | 5 | Dizziness | Constant | 1 | Possibly | None | Recovered |
|   |   |   | 5 | Elevated BP | Intermittent | 1 | Possibly | None | Recovered |
|   |   |   | 5 | Headache | Constant | 1 | Possibly | None | Recovered |
|   |   |   | 5 | Tachycardia | Intermittent | 1 | Possibly | None | Recovered |
|   |   |   | 5 | Pharyngitis | Constant | 1 | Unrelated | None | Recovered |
|   |   |   | 5 | Nausea | x1 | 1 | Possibly | None | Recovered |
| 1100 mg | 24 | F/33 | 1 | Heartburn | Constant | 1 | Possibly | None | Recovered |
|   |   |   | 3 | Constipation | Constant | 1 | Possibly | None | Recovered |
|   | 28 | M/32 | 7 | Skin Irritation | Constant | 1 | Unlikely | None | Recovered |
|   | 31 | F/50 | 5 | Constipation | Constant | 1 | Possibly | None | Recovered |
|   |   |   | 6 | Heartburn | Constant | 1 | Possibly | None | Recovered |
|   | 38 | F/34 | 1 | Nausea | x1 | 1 | Unlikely | None | Recovered |
|   |   |   | 5 | Nausea | Constant | 1 | Possibly | None | Recovered |
|   |   |   | 6 | Nausea | Constant | 1 | Possibly | None | Recovered |
|   |   |   | 6 | Dizziness | Constant | 1 | Possibly | None | Recovered |
|   | 39 | M/38 | 1 | Viral URI | Constant | 1 | Unlikely | None | Recovered |
|   |   |   | 1 | Dizziness | x1 | 1 | Possibly | None | Recovered |
|   |   |   | 1 | Nausea | x1 | 1 | Possibly | None | Recovered |
| 1650 mg | 44 | F/49 | 1 | Heartburn | Constant | 1 | Possibly | Ranitidine | Recovered |
|   |   |   | 2 | Constipation | Constant | 1 | Unlikely | None | Recovered |
|   |   |   | 3 | Headache | Transient | 1 | Possibly | None | Recovered |
|   |   |   | 3 | Nausea | x1 | 1 | Possibly | None | Recovered |
|   |   |   | 4 | Nausea | Constant | 1 | Possibly | None | Recovered |
|   |   |   | 4 | Headache | Constant | 1 | Possibly | None | Recovered |
|   |   |   | 5 | Dizziness | Constant | 1 | Possibly | None | Recovered |
|   |   |   | 5 | Vomiting | x1 | 1 | Possibly | None | Recovered |
|   |   |   | 6 | Dysuria | Intermittent | 1 | Unrelated | None | Recovered |
|   |   |   | 6 | Nausea | Constant | 2 | Possibly | None | Recovered |
|   |   |   | 6 | Vomiting | x1 | 2 | Possibly | IV Fluids | Recovered |
|   | 47 | M/30 | 1 | Nausea | x1 | 1 | Possibly | None | Recovered |
|   | 50 | M/43 | 3 | Constipation | Constant | 1 | Unlikely | None | Recovered |
|   |   |   | 3 | Nausea | Constant | 1 | Possibly | None | Recovered |
|   |   |   | 4 | Nausea | Constant | 1 | Possibly | None | Recovered |
|   |   |   | 6 | Heartburn | Constant | 1 | Possibly | Ranitidine | Recovered |
|   |   |   | 6 | Dizziness | Constant | 1 | Possibly | None | Recovered |
|   |   |   | 6 | Nausea | Constant | 1 | Possibly | None | Recovered |
|   |   |   | 6 | Vomiting | x1 | 1 | Possibly | None | Recovered |

TABLE 7-continued

CEM-102 Multiple-Dose Treatment-Emergent Adverse Events (Blinded)

| Cohort/ Treatment | Subject # | Gender Age (Y) | Day | Adverse Event | Frequency | Severity Grade | Relationship | Treatment | Outcome |
|---|---|---|---|---|---|---|---|---|---|
| | 59 | F/31 | 3 | Paresthesia | Constant | 1 | Possibly | None | Recovered |
| | | | 4 | Constipation | Constant | 1 | Unlikely | None | Recovered |
| | | | 5 | Vomiting | x1 | 1 | Possibly | None | Recovered |
| | 60 | M/46 | 3 | Dizziness | Constant | 1 | Possibly | None | Recovered |
| | | | 3 | Headache | Constant | 1 | Possibly | None | Recovered |
| | | | 3 | Loose stools | x1 | 1 | Possibly | None | Recovered |
| | | | 3 | Nausea | Constant | 1 | Possibly | None | Recovered |
| | | | 3 | Paresthesia | Transient | 1 | Possibly | None | Recovered |
| | | | 3 | Weakness | Constant | 1 | Possibly | None | Recovered |
| | | | 4 | Headache | Constant | 1 | Possibly | None | Recovered |
| | | | 5 | Nausea | Constant | 1 | Possibly | None | Recovered |
| | | | 5 | Paresthesia | Constant | 1 | Possibly | None | Recovered |
| | | | 5 | Vomiting | x1 | 1 | Possibly | None | Recovered |
| | | | 6 | Loose stools | Multiple | 1 | Possibly | None | Recovered |
| | | | 6 | Nausea | Constant | 1 | Possibly | None | Recovered |
| | | | 6 | Paresthesia | Constant | 1 | Possibly | None | Recovered |
| | | | 6 | Vomiting | X1 | 1 | Possibly | None | Recovered |
| | | | 7 | Nausea | Constant | 1 | Possibly | None | Recovered |
| | | | 7 | Paresthesia | Constant | 1 | Possibly | None | Recovered |

Figure 5:
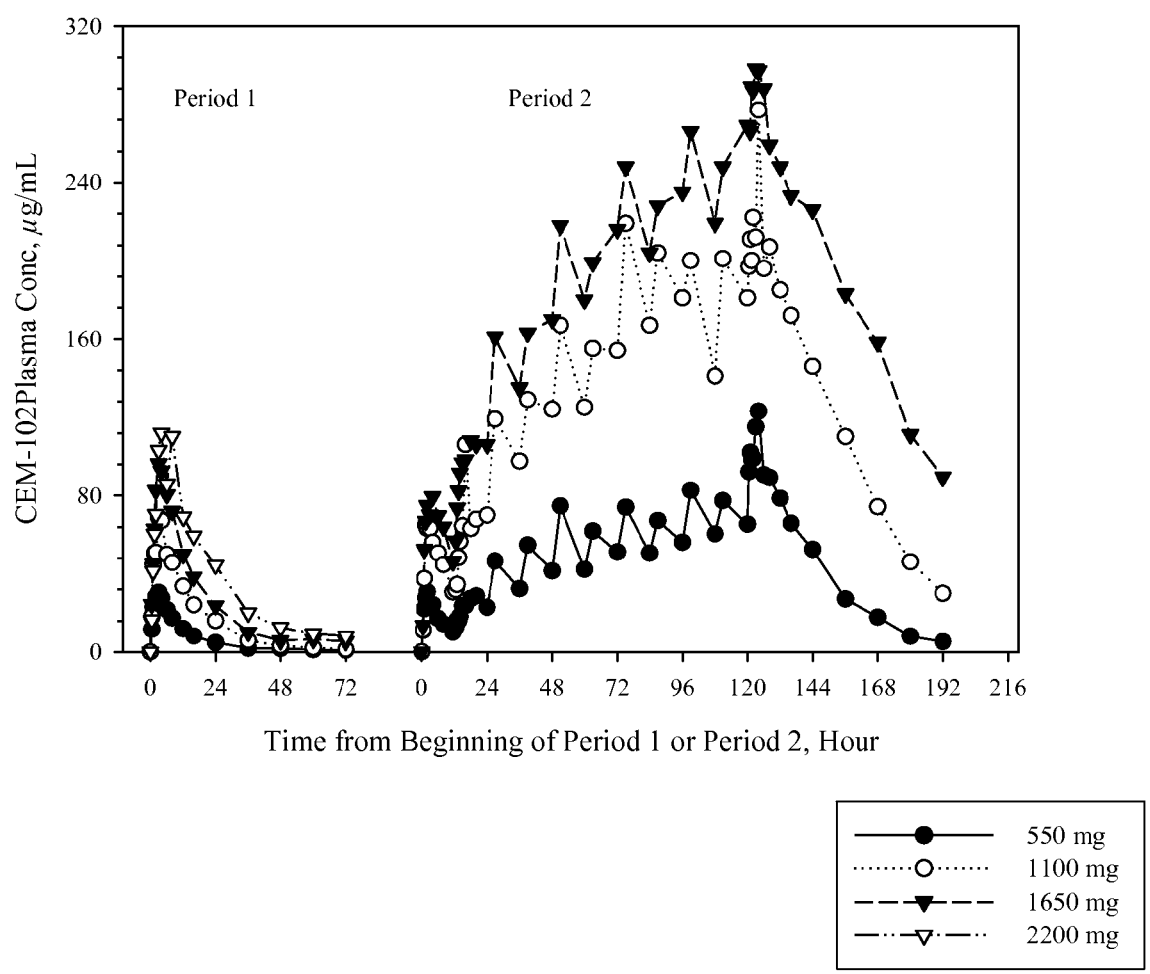
FIG. 5—Mean CEM-102 (Sodium fusidate) single and multiple dose plasma concentrations (linear scale). Cohort 1 (550 mg), cohort 2 (1100 mg), cohort 3 (1650 mg), and cohort 4 (2200 mg—single dose only).

PK results from single and multiple dose administration of CEM-102 are shown in Table 8 and FIG. 5.

TABLE 8

CEM-102 Single and Multiple Dose Pharmacokinetic Parameters

| | Single and Multiple Dose Groups | | | | | | Single Dose Only | |
|---|---|---|---|---|---|---|---|---|
| | Cohort 1 550 mg | | Cohort 2 1100 mg | | Cohort 3 1650 mg | | Cohort 4 2200 mg | |
| Parameter | Mean | SD | Mean | SD | Mean | SD | Mean | SD |
| Period 1 Day 1 | | | | | | | | |
| $C_{max}$, µg/mL | 33.4 | 12.2 | 72.2 | 10.8 | 102 | 25.8 | 128 | 28.3 |
| $T_{max}$, h[a] | 2.00 | (2-3) | 3.50 | (1-4) | 3.00 | (2-4) | 6.00 | (3-8) |
| $K_{el}$, h$^{-1}$[b] | 0.0564 | 0.0130 | 0.0617 | 0.0120 | 0.0498 | 0.0151 | 0.0500 | 0.0159 |
| $T_{1/2}$, h[c] | 12.3 | 2.98 | 11.2 | 2.17 | 13.9 | 4.29 | 13.9 | 4.52 |
| $AUC_{(0-24)}$, µg · h/mL | 242 | 102 | 844 | 115 | 1,260 | 386 | 1,690 | 427 |
| $AUC_{(0-inf)}$, µg · h/mL | 441 | 269 | 1,100 | 247 | 1,800 | 689 | 2,650 | 978 |
| CL/F, L/h | 1.69 | 1.00 | 1.04 | 0.202 | 1.07 | 0.519 | 0.924 | 0.434 |
| $V_d$/F, L | 28.4 | 10.8 | 16.9 | 1.20 | 21.1 | 4.96 | 19.2 | 6.38 |
| Period 2 Day 6 | | | | | | | | |
| $C_{max}$, µg/mL | 130 | 30.5 | 281 | 52.5 | 324 | 26.8 | — | — |
| $T_{max}$, h[a] | 3.00 | (1.5-4) | 4.00 | (4-8) | 4.00 | (1.5-6) | — | — |
| $K_{el}$, h$^{-1}$[b] | 0.0554 | 0.0131 | 0.0404 | 0.0162 | 0.0199 | 0.0118 | — | — |
| $T_{1/2}$, h[c] | 12.5 | 3.05 | 17.1 | 6.79 | 31.6 | 18.9 | — | — |
| $AUC_{(0-12)}$, µg · h/mL | 1,150 | 433 | 2,530 | 417 | 3290 | 146 | — | — |
| CL/F, L/h | 0.553 | 0.255 | 0.449 | 0.100 | 0.0503 | 0.0223 | — | — |
| $V_d$/F, L | 9.88 | 3.05 | 12.7 | 5.66 | 34.8 | 22.9 | — | — |
| $C_{max}$ accumulation ratio[d] | 3.89 | — | 3.89 | — | 3.18 | — | — | — |
| $AUC_{(0-12)}$ accumulation ratio[e] | 2.61 | — | 2.30 | — | 1.83 | — | — | — |

[a]Expressed as median and range
[b]Apparent first-order terminal elimination rate constant
[c]Expressed as harmonic mean and pseudo SD
[d]Mean $C_{max}$ Day 6/Mean $C_{max}$ Day 1
[e]Mean $AUC_{(0-12)}$ Day 6/Mean $AUC_{(0-inf)}$ Day 1

As shown in FIG. 5, the increases in $C_{max}$ and AUC appear to be more than dose proportional from the 550 mg to the 1100 mg dose, but then approximately dose proportional from the 1100 mg to the 2200 mg dose (only single doses). In the 550 to 1650 mg dose groups CEM-102 demonstrated higher PK exposures after 5.5 days of dosing in Period 2 compared to a single dose on Day 1 in Period 1, indicating that accumulation occurs over the dosing period.

The protocol was amended for assessment of the safety, tolerability, and PK of front-loaded dose regimens comprised of a higher dose of CEM-102 on Day 1 followed by lower doses for the subsequent 6.5 days. All loading dose regimens employed multiple doses lower than the maximum tolerated dose (MTD) established in the first part of the study (1650 mg administered as multiple doses).

The loading dose regimens assessed were 1100 mg BID on Day 1 and 550 mg BID on the following 6.5 days in Period 2 of Cohort 4 and 1650 mg BID on Day 1 and 825 mg BID on the following 6.5 days in Cohort 5.

Four AEs, all mild in severity, were reported by 3 subjects that received loading dose regimens (Table 9). One subject in the 1100/550 mg group reported nausea on the first day of dosing only. No gastrointestinal AEs were reported in the 1650/825 mg group.

TABLE 9

CEM-102 Loading-Dose Regimens Treatment-emergent Adverse Events

| Dose Group | Treatment Group | Subj # | M/F Age (Y) | Day | Adverse Event | Freq. | Sev Grade | Relation | Treatment | Outcome |
| --- | --- | --- | --- | --- | --- | --- | --- | --- | --- | --- |
| 1100/550 mg | CEM-102 | 080 | F/21 | 1 | Urinary frequency | Constant | 1 | Possibly | None | Recovered |
|  |  |  |  | 1 | Nausea | Constant | 1 | Possibly | None | Recovered |
|  | CEM-102 | 081 | F/54 | 2 | Constipation | Constant | 1 | Unlikely | Fruit juice | Recovered |
| 1650/825 mg | CEM-102 | 087 | F/24 | 6 | Redness to face | Constant | 1 | Unrelated | None | Recovered |

There were no clinically significant changes in physical examinations, vital signs, ECGs, or laboratory parameters after either loading dose regimen.

Figure 6:
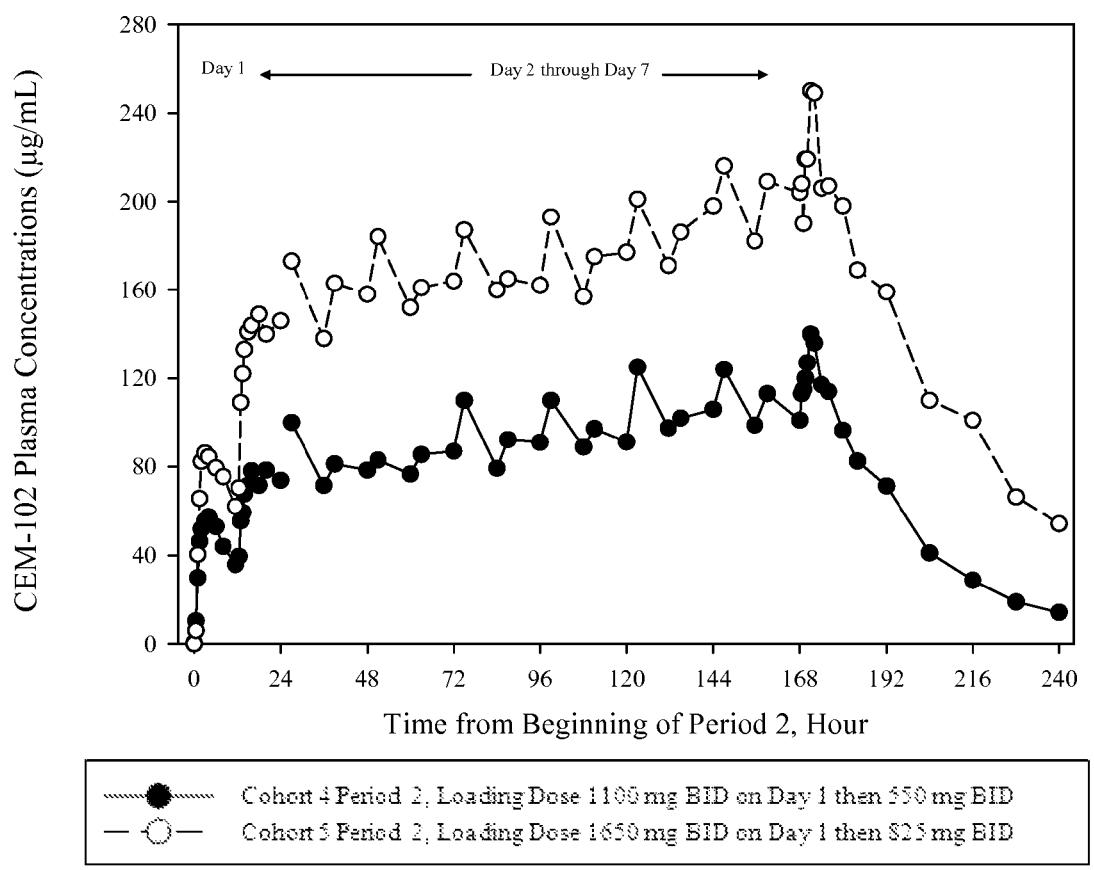
FIG. 6—Mean CEM-102 (Sodium fusidate) plasma concentrations in loading dose regimens (linear scale).
Figure 7:
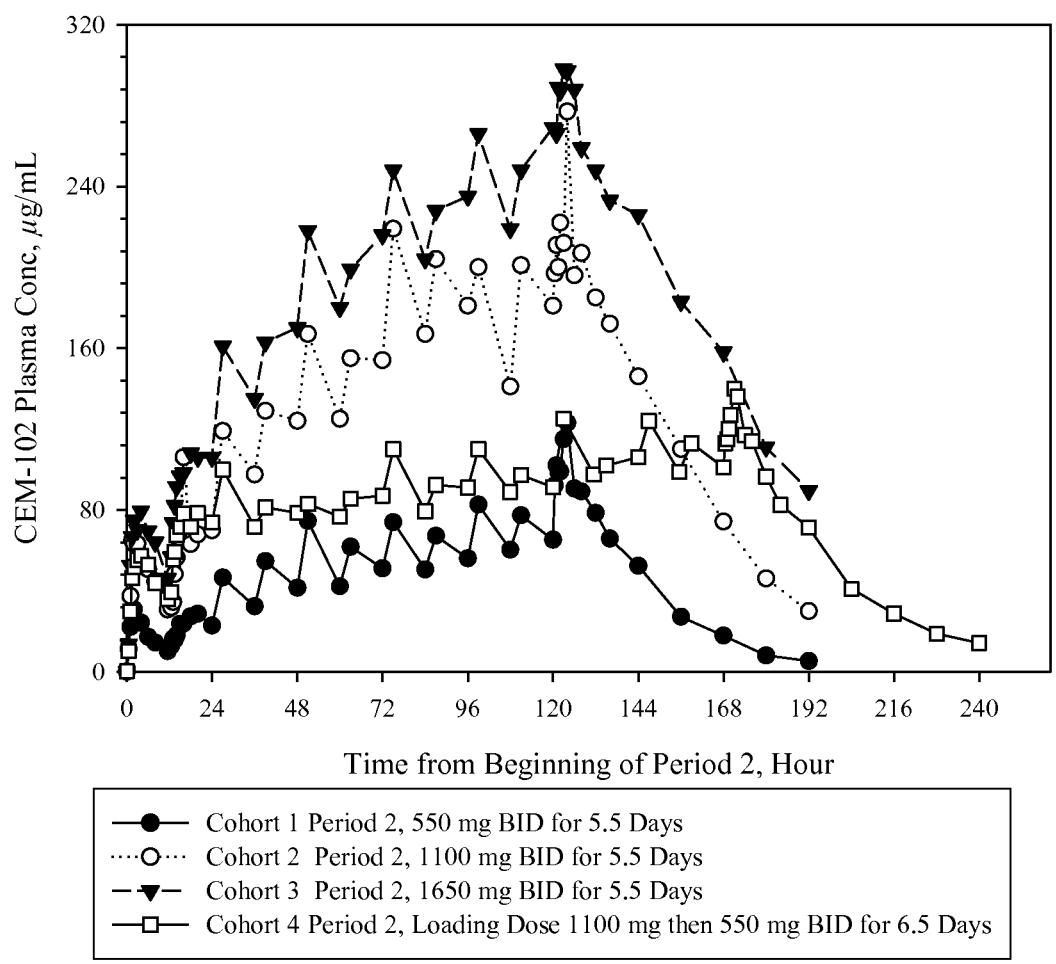
FIG. 7—Mean CEM-102 (Sodium fusidate) multiple dose plasma concentrations (linear scale) which is a compilation of the Period 2 data of FIG. 5 and the Cohort 4, Period 2, data of FIG. 6.

PK results of the loading dose regimens are shown in FIG. 6. The 1100 mg BID loading dose followed by 550 mg BID for 6.5 days resulted in a mean trough plasma concentration of approximately 74 µg/mL at 24 hours and approximately 105 µg/mL after 7 days of dosing. The 1650 mg BID loading dose followed by 825 mg BID for 6.5 days resulted in a mean trough plasma concentration of approximately 150 µg/mL at 24 hours and approximately 200 µg/mL after 7 days of dosing. FIG. 7 is a compilation of the period 2 portion of FIG. 5 and the 1100/550 mg BID loading dose regimen data. FIG. 7 demonstrates that, in contrast with the conventional BID regimens, near steady state plasma concentrations are reached at 24 hours after the first dose on Day 1 and these plasma concentrations are maintained at or above this level throughout the remainder of the 7 day treatment course.

The results demonstrated that CEM-102 was safe and well tolerated in single doses up to 2200 mg, with a threshold for symptoms of gastrointestinal intolerance between 1650 mg and 2200 mg. CEM-102 administered in doses up to 1650 mg BID for 5.5 days was safe and generally well tolerated; however, as 4 subjects had vomiting at the 1650 mg dose level, escalation to the 2200 mg dose level was limited to single doses. AEs appeared to be related to dose and duration of exposure, with gastrointestinal symptoms reported more frequently after 3-5 days of dosing and at higher doses. Loading dose regimens of CEM-102 1100/550 mg and 1650/825 mg for a total of 7.5 days were very well tolerated. Loading dose regimens appeared to be generally better tolerated than the conventional BID dosing regimens for similar levels of overall plasma exposure. There were no clinically significant changes in physical examinations, vital signs, ECGs, or laboratory parameters after single doses of CEM-102 up to 2200 mg, multiple doses up to 1650 mg for 5.5 days, or loading dose regimens of 1100/500 mg or 1650/825 mg for a total of 7.5 days.

The study revealed the following information concerning pharmacokinetics associated with FA administration to humans using the noted dosing regimens. $C_{max}$ and AUC showed more than dose proportional increases from 550 mg to 1100 mg, then approximately dose proportional increases from 1100 to 2200 mg (single dose only for 2200 mg). Accumulation of CEM-102 occurred from Day 1 to Day 6 of dosing at all dose levels. The 1100 mg BID loading dose followed by a 550 mg BID maintenance dose resulted in mean trough plasma concentrations of approximately 74 µg/mL at 24 hours and approximately 105 µg/mL after 7 days of dosing. The 1650 mg BID loading dose followed by an 825 mg BID maintenance dose resulted in mean trough plasma concentrations of approximately 150 µg/mL at 24 hours and approximately 200 µg/mL after 7 days of dosing. The loading dose regimens produced plasma concentrations that approached steady-state levels at 24 hours and appeared to be better tolerated than the conventional BID regimens for comparable levels of overall exposure.

The data shows that a loading dose between 1100 mg BID-1650 mg BID is sufficient to give a substantial blood level to provide multiples of the MIC against *S. aureus* and beta hemolytic streptococci. These high blood levels are sufficient to inhibit the bacterium as well as to prevent the selection of resistant bacteria. Keeping the growth to below detectable levels for a period of 72 hours without selection of resistant strains has been noted to be sufficient time in which to allow for clearance by neutrophils and macrophages, and it is sufficient to prevent the selection of resistant strains (Louie et al., *Antimicrob. Agents Chemother.* 52:2486-2496 (2008)). Thus, after the loading dose, the 600 mg as the maintenance dose was sufficient to maintain a steady state level of 80 micrograms per ml throughout the dosing period.

Example 7

Pharmacodynamics of CEM-102 Against Methicillin-Resistant *Staphylococcus aureus* Using In vitro Models A hollow fiber model was used to evaluate CEM-102 resistance potential in methicillin-resistant *S. aureus* (MRSA) strain USA 300 (Network of Antimicrobial Resistance in *Staphylococcus aureus* (NARSA), Chantilly, Va.). USA 300 is a highly virulent strain of MRSA and is the most common community-associated MRSA isolate in the USA. MIC values were determined in accordance with Clinical and Laboratory Standards Institute (CLSI).

The hollow fiber model comprised a two-compartment hollow fiber model (Louie et al. *Antimicrob Agents Chemother* 52:2486-2496(2008)) consisting of a volume of 15 mL in the central compartment, with multiple ports for the removal of broth, delivery of antibiotics, and collection of bacterial and antimicrobial samples. A peristaltic pump was used to continually replace antibiotic-containing medium with fresh media (Mueller Hinton Broth, supplemented with calcium, magnesium, and human albumin to a final concentration of 4 g/dL, simulating human physiologic levels) at a rate to simulate the half-life of CEM-102 based on human PK data. All experiments were performed in duplicate.

Hollow fibers contain 15 ml of media was prepared and inoculated with $10^6$ colony forming units (CFU)/mL USA 300 bacteria. One of three different dosing regimens of CEM-120 was then applied to the fibers: (1) 600 mg/ml q12h; (2) 1200 mg/ml×2, followed by 600 mg/ml, q12h; (3) 1500 mg/ml×2, followed by 600 mg/ml, q12h.

On Days 0, 1, 2, 3, 4, 5, 6, 7, 8, 9 and 10 samples were withdrawn from the fibers and plated on media with no-drug (TSA II with 5% sheep blood) or drug-containing agar (brain heart infusion), consisting of 4, 8, 16×MIC of CEM-102 (1 ug/ml, 2 ug/ml, 4.0 ug/ml, respectively; MIC=0.25 ug/ml).

Figure 8:
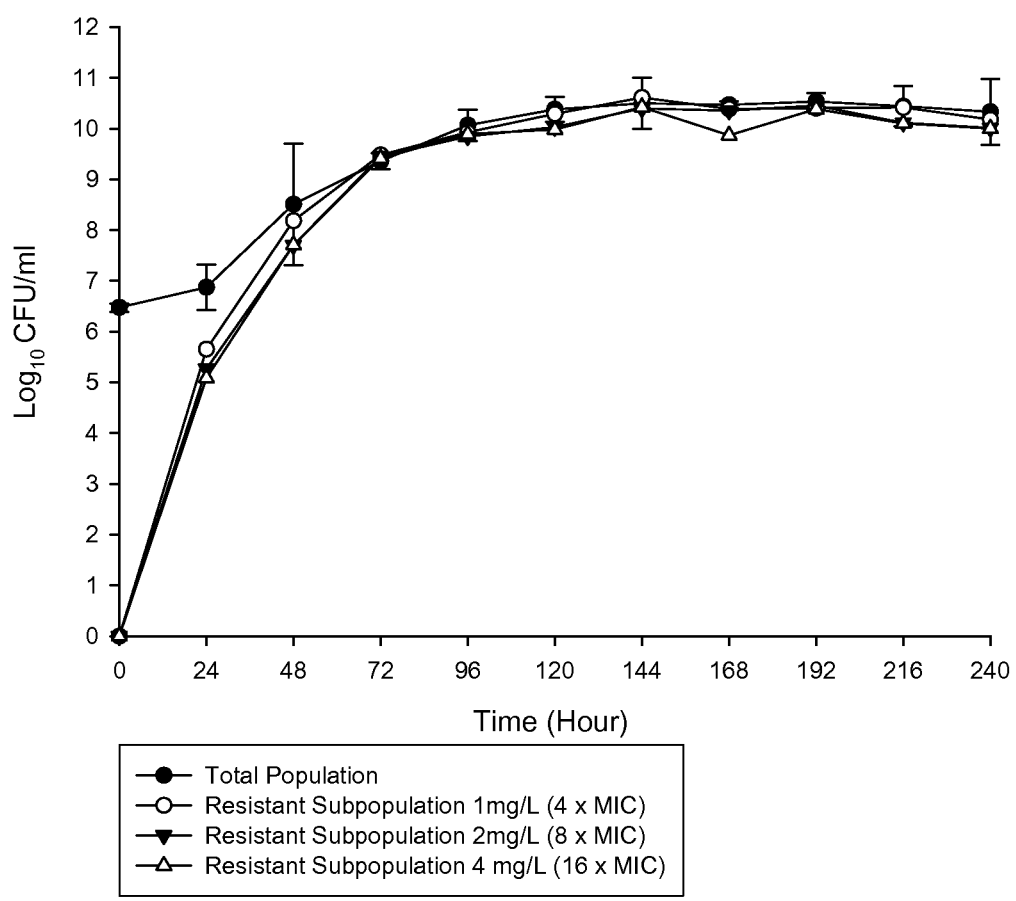
FIG. 8—CEM-102 pharmacodynamics in hollow fiber. CEM-102 (Sodium fusidate) 600 mg q12h vs. USA 300.

FIG. 8 shows the growth of samples withdrawn from 600 mg/ml q12h fibers at the different time points on plates without CEM-102 (solid circles), with 1 ug/ml CEM-102 (open circles), with 2 ug/ml CEM-102 (solid triangle), and with 4 ug/ml CEM-102 (open triangle). The results in FIG. 8 show that treatment using 600 mg FA q12h resulted in regrowth and development of resistance by 24 h and 48 h.

Figure 9:
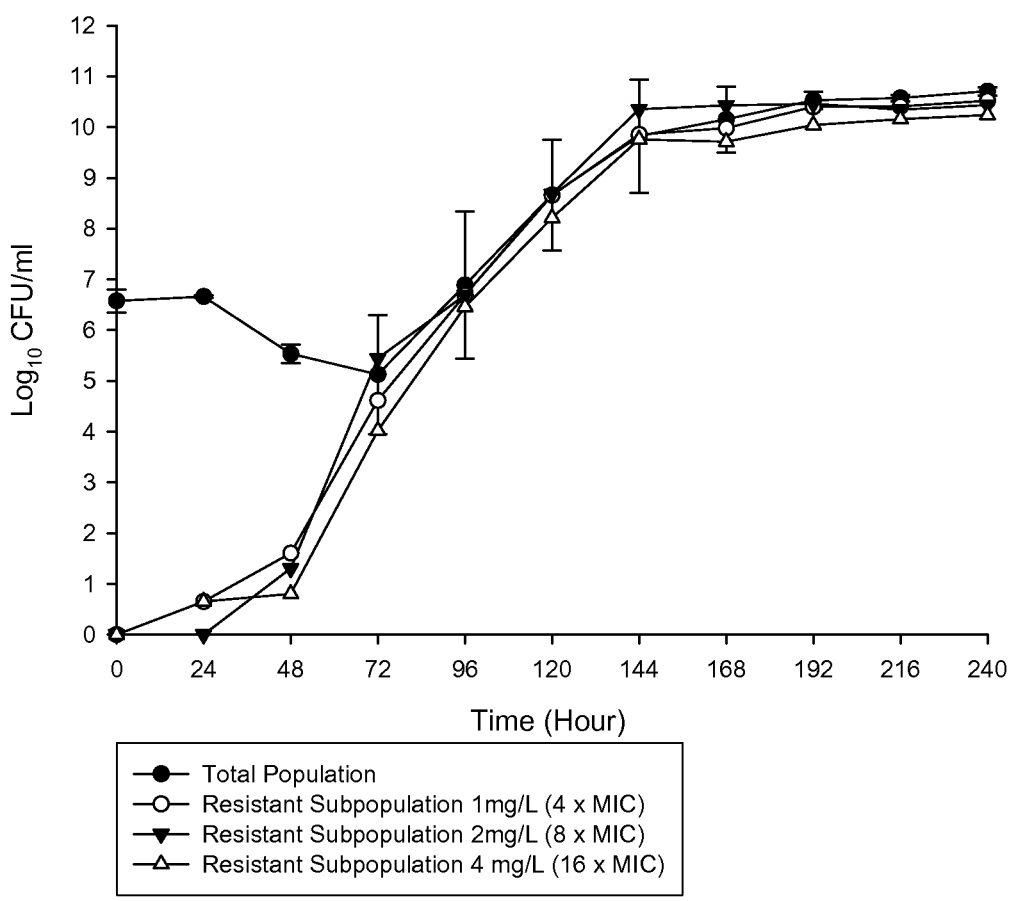
FIG. 9—CEM-102 pharmacodynamics in hollow fiber. CEM-102 (Sodium fusidate) 1200 mg×2 then 600 mg q12h vs. USA 300.

FIG. 9 shows the growth of samples withdrawn from 1200 mg/ml×2, 600 mg/ml, q12h, fibers at the different time points on plates without CEM-102 (solid circles), with 1 ug/ml CEM-102 (open circles), with 2 ug/ml CEM-102 (solid triangle), and with 4 ug/ml CEM-102 (open triangle). The results in FIG. 9 show that treatment using 1200 mg×2 then 600 mg q12h suppressed bacterial counts and reduced bacterial counts by 2 logs, with rebound at 72 h.

Figure 10:
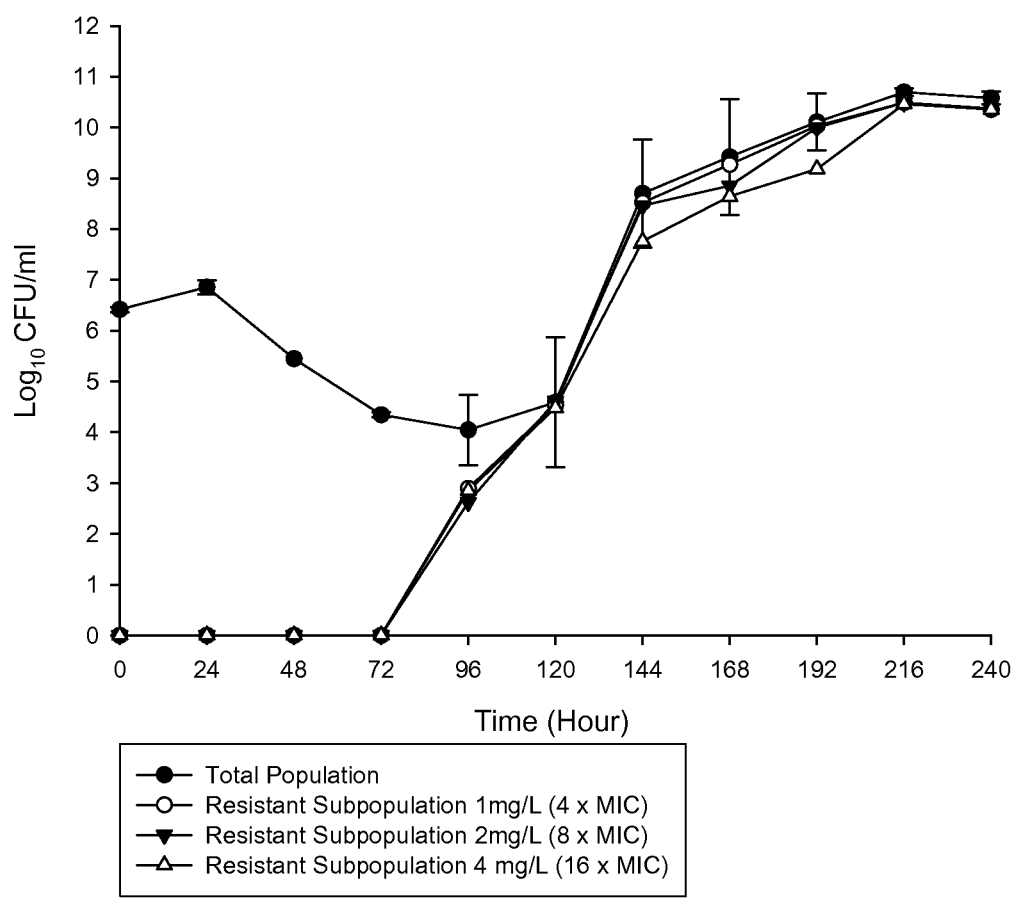
FIG. 10—CEM-102 pharmacodynamics in hollow fiber. CEM-102 (Sodium fusidate) 1500 mg×2 then 600 mg q12h vs. USA 300.

FIG. 10 shows the growth of samples withdrawn from 1500 mg/ml×2, 600 mg/ml, q12h, fibers at the different time points on plates without CEM-102 (solid circles), with 1 ug/ml CEM-102 (open circles), with 2 ug/ml CEM-102 (solid triangle), and with 4 ug/ml CEM-102 (open triangle). The results in FIG. 10 show that treatment using 1500 mg×2 then 600 mg q12h suppressed resistance until >72h and resulted in killing over 2.5 log and even approached the threshold of bactericidal activity, and rebounded at 144 h.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of treating a bacterial infection in a subject, comprising:
    (a) administering at least one loading dose of a pharmaceutical composition comprising fusidic acid, or a pharmaceutically acceptable salt thereof, to a subject in need of treatment, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 24 hours and a minimum trough plasma concentration of fusidic acid of not less than about 50 ug/ml, and
    (b) administering at least one maintenance dose of a pharmaceutical composition comprising fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

2. The method of claim 1, wherein the $C_{max}$ is not less than about 80 ug/ml, the minimum trough plasma concentration of (a) is not less than about 60 ug/ml and the minimum trough plasma concentration of (b) is not less than about 70 ug/ml.

3. The method of claim 1, wherein the $C_{max}$ is not less than about 100 ug/ml, the minimum trough plasma concentration of (a) is not less than about 80 ug/ml and the minimum trough plasma concentration of (b) is not less than about 80 ug/ml.

4. The method of claim 1, wherein the total loading dose administered in (a) is between about 2000 mg and about 3600 mg.

5. The method of claim 1, wherein the at least one loading dose of (a) comprises two loading doses, and wherein the second loading dose is administered about 12 hours after administration of the first loading dose, and wherein each loading dose is between about 1000 mg and about 1850 mg.

6. The method of claim 1, wherein the at least one maintenance dose of (b) comprises multiple maintenance doses of independently between about 500 mg and 1000 mg administered about 12 hours apart, beginning about 12 hours after administration of the loading dose.

7. The method of claim 1, wherein the at least one loading dose of (a) comprises two loading doses, wherein each loading dose is independently between about 1000 mg and about 1850 mg, and wherein the second loading dose is administered about 12 hours after administration of the first loading dose; and
    wherein the administering of (b) comprises multiple maintenance doses of independently between about 500 mg and 1000 mg about 12 hours apart, beginning about 12 hours after administration of the second loading dose.

8. The method of claim 7, wherein each loading dose is independently at least about 1500 mg.

9. The method of claim 7, wherein each maintenance dose is independently at least about 600 mg.

10. The method of claim 1, wherein the minimum trough plasma concentration of not less than about 50 ug/ml is maintained for at least about 48 hours after the administering of (a).

11. The method of claim 1, wherein the minimum trough plasma concentration of not less than about 50 ug/ml is maintained for at least about 72 hours after the administering of (a).

12. The method of claim 1, wherein the minimum trough plasma concentration of not less than about 50 ug/ml is maintained for at least about 96 hours after the administering of (a).

13. The method of claim 1, wherein the subject is a human.

14. The method of claim 1, wherein the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species.

15. The method of claim 1, wherein the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthra-*

*cis, Bordetella pertussis, Clostridium difficile, Enterococcus faecalis, Enterococcus faecium* and *Corynebacterium diphtheriae.*

16. The method of claim 1, wherein the bacterial infection is an infection caused by *Enterococcus faecalis.*

17. The method of claim 1, wherein the bacterial infection is an infection caused by *Enterococcus faecium.*

18. The method of claim 1, wherein the bacterial infection is an infection selected from the group consisting of a skin and soft tissue infection, a bone infection, a joint infection, pneumonia, a wound infection, a burn infection, an infection of the blood, and an infection associated with cystic fibrosis.

19. The method of claim 1, wherein the pharmaceutical composition comprising fusidic acid, or a pharmaceutically acceptable salt thereof, is in the form of a tablet, a capsule, an IV solution, an inhalable formulation, a powder formulation, or a formulated suspension.

20. The method of claim 1, wherein the pharmaceutical composition comprising fusidic acid, or a pharmaceutically acceptable salt thereof, is administered orally, by injection or by intravenous infusion.

21. The method of claim 1, wherein the subject does not experience an adverse level of nausea.

22. A method of treating a bacterial infection in a subject, comprising:
(a) administering at least one loading dose of a pharmaceutical composition comprising fusidic acid, or a pharmaceutically acceptable salt thereof, to a subject in need of treatment in an amount sufficient to achieve a minimum plasma concentration of not less than about 50 ug/ml fusidic acid within 24 hours, and
(b) administering at least one maintenance dose of a pharmaceutical composition comprising fusidic acid, or a pharmaceutically acceptable salt thereof, to the subject of (a) in an amount sufficient to maintain a minimum plasma concentration of not less than about 50 ug/ml fusidic acid for at least about 24 hours after the administering of (a).

23. The method of claim 22, wherein a minimum plasma concentration of fusidic acid of not less than about 60 ug/ml is achieved in (a) and a minimum plasma concentration of fusidic acid of not less than about 60 ug/ml is maintained in (b).

24. The method of claim 22, wherein a minimum plasma concentration of fusidic acid of not less than about 80 ug/ml is achieved in (a) and a minimum plasma concentration of fusidic acid of not less than about 80 ug/ml is maintained in (b).

25. The method of claim 22, wherein the total loading dose administered in (a) is between about 2000 mg and about 3600 mg.

26. The method of claim 22, wherein the at least one loading dose of (a) comprises two loading doses, wherein the second loading dose is administered about 12 hours after administration of the first loading dose, and wherein each loading dose is between about 1000 mg and about 1850 mg.

27. The method of claim 22, wherein the at least one maintenance dose of (b) comprises multiple maintenance doses of independently between about 500 mg and 1000 mg administered about 12 hours apart, beginning about 12 hours after administration of the loading dose.

28. The method of claim 22, wherein the at least one loading dose of (a) comprises two loading doses, wherein each loading dose is independently between about 1000 mg and about 1850 mg, and wherein the second loading dose is administered about 12 hours after administration of the first loading dose; and wherein the administering of (b) comprises multiple maintenance doses of independently between about 500 mg and 1000 mg about 12 hours apart, beginning about 12 hours after administration of the second loading dose.

29. The method of claim 28, wherein each loading dose is independently at least about 1500 mg.

30. The method of claim 28, wherein each maintenance dose is independently at least about 600 mg.

31. The method of claim 22, wherein the minimum plasma concentration of not less than about 50 ug/ml is maintained for at least about 48 hours after the administering of (a).

32. The method of claim 22, wherein the minimum plasma concentration of not less than about 50 ug/ml is maintained for at least about 72 hours after the administering of (a).

33. The method of claim 22, wherein the minimum plasma concentration of not less than about 50 ug/ml is maintained for at least about 96 hours after the administering of (a).

34. The method of claim 22, wherein the subject is a human.

35. The method of claim 22, wherein the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species.

36. The method of claim 22, wherein the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae.*

37. The method of claim 22, wherein the bacterial infection is an infection caused by *Enterococcus faecalis.*

38. The method of claim 22, wherein the bacterial infection is an infection caused by *Enterococcus faecium.*

39. The method of claim 22, wherein the bacterial infection is an infection selected from the group consisting of a skin and soft tissue infection, a bone infection, a joint infection, pneumonia, a wound infection, a burn infection, an infection of the blood, and an infection associated with cystic fibrosis.

40. The method of claim 22, wherein the pharmaceutical composition comprising fusidic acid, or a pharmaceutically acceptable salt thereof, is in the form of a tablet, a capsule, an IV solution, an inhalable formulation, a powder formulation, or a formulated suspension.

41. The method of claim 22, wherein the pharmaceutical composition comprising fusidic acid, or a pharmaceutically acceptable salt thereof, is administered orally, by injection or by intravenous infusion.

42. The method of claim 22, wherein the subject does not experience an adverse level of nausea.

43. A method of treating a bacterial infection in a subject, comprising:
(a) administering a first and a second loading dose of a pharmaceutical composition comprising fusidic acid, or a pharmaceutically acceptable salt thereof, to a subject in need of treatment, wherein each loading dose is independently between about 1000 mg and about 1850 mg, and wherein the second loading dose is administered about 12 hours after the first loading dose; and
(b) administering two or more maintenance doses of a pharmaceutical composition comprising fusidic acid, or a pharmaceutically acceptable salt thereof, to the subject of (a), wherein each maintenance dose is independently between about 500 mg and 1000 mg, wherein a first maintenance dose is administered about 12 hours after administration of the second loading dose, and wherein subsequent maintenance doses are administered about 12 hours apart.

44. The method of claim 43, wherein each loading dose is independently at least about 1500 mg.

45. The method of claim 43, wherein each maintenance dose is independently at least about 600 mg.

46. The method of claim 43, wherein at least three maintenance doses are administered in (b).

47. The method of claim 43, wherein at least four maintenance doses are administered in (b).

48. The method of claim 43, wherein at least five maintenance doses are administered in (b).

49. The method of claim 43, wherein at least six maintenance doses are administered in (b).

50. The method of claim 43, wherein the subject is a human.

51. The method of claim 43, wherein the bacterial infection is an infection caused by bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species.

52. The method of claim 43, wherein the bacterial infection is an infection caused by bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*.

53. The method of claim 43, wherein the bacterial infection is an infection caused by *Enterococcus faecalis*.

54. The method of claim 43, wherein the bacterial infection is an infection caused by *Enterococcus faecium*.

55. The method of claim 43, wherein the bacterial infection is an infection selected from the group consisting of a skin and soft tissue infection, a bone infection, a joint infection, pneumonia, a wound infection, a burn infection, an infection of the blood, and an infection associated with cystic fibrosis.

56. The method of claim 43, wherein the pharmaceutical composition comprising fusidic acid, or a pharmaceutically acceptable salt thereof, is in the form of a tablet, a capsule, an IV solution, an inhalable formulation, a powder formulation, or a formulated suspension.

57. The method of claim 43, wherein the pharmaceutical composition comprising fusidic acid, or a pharmaceutically acceptable salt thereof, is administered orally, by injection or by intravenous infusion.

58. The method of claim 43, wherein the subject does not experience an adverse level of nausea.

59. A method of reducing development of an antibiotic-resistant strain of bacteria in a subject having a bacterial infection, comprising:
(a) administering at least one loading dose of a pharmaceutical composition comprising fusidic acid, or a pharmaceutically acceptable salt thereof, to a subject having a bacterial infection, in an amount sufficient to reach a pharmacokinetic (PK) profile for fusidic acid comprising a maximum plasma concentration ($C_{max}$) of fusidic acid of not less than about 70 ug/ml, a time to maximum plasma concentration ($T_{max}$) of fusidic acid of no more than about 20 hours and a minimum trough plasma concentration of fusidic acid of not less than about 50 ug/ml, and
(b) administering at least one maintenance dose of a pharmaceutical composition comprising fusidic acid, or a pharmaceutically acceptable salt thereof, to the subject of (a) in an amount sufficient to maintain a minimum trough plasma concentration of fusidic acid of not less than about 50 ug/ml for at least about 24 hours after the administering of (a).

60. The method of claim 59, wherein the $C_{max}$ is not less than about 80 ug/ml, the minimum trough plasma concentration of (a) is not less than about 60 ug/ml and the minimum trough plasma concentration of (b) is not less than about 70 ug/ml.

61. The method of claim 59, wherein the $C_{max}$ is not less than about 100 ug/ml, the minimum trough plasma concentration of (a) is not less than about 80 ug/ml and the minimum trough plasma concentration of (b) is not less than about 80 ug/ml.

62. The method of claim 59, wherein the total loading dose administered in (a) is between about 2000 mg and about 3600 mg.

63. The method of claim 59, wherein the at least one loading dose of (a) comprises two loading doses, and wherein the second loading dose is administered about 12 hours after administration of the first loading dose, and wherein each loading dose is between about 1000 mg and about 1850 mg.

64. The method of claim 59, wherein the at least one maintenance dose of (b) comprises multiple maintenance doses of independently between about 500 mg and 1000 mg administered about 12 hours apart, beginning about 12 hours after administration of the loading dose.

65. The method of claim 59, wherein the at least one loading dose of (a) comprises two loading doses, wherein each loading dose is independently between about 1000 mg and about 1850 mg, and wherein the second loading dose is administered about 12 hours after administration of the first loading dose; and
wherein the administering of (b) comprises multiple maintenance doses of independently between about 500 mg and 1000 mg about 12 hours apart, beginning about 12 hours after administration of the second loading dose.

66. The method of claim 65, wherein each loading dose is independently at least about 1500 mg.

67. The method of claim 65, wherein each maintenance dose is independently at least about 600 mg.

68. The method of claim 59, wherein the minimum trough plasma concentration of not less than about 50 ug/ml is maintained for at least about 48 hours after the administering of (a).

69. The method of claim 59, wherein the minimum trough plasma concentration of not less than about 50 ug/ml is maintained for at least about 72 hours after the administering of (a).

70. The method of claim 59, wherein the minimum trough plasma concentration of not less than about 50 ug/ml is maintained for at least about 96 hours after the administering of (a).

71. The method of claim 59, wherein the subject is a human.

72. The method of claim 59, wherein the bacterial infection is an infection caused by a bacteria selected from the group consisting of staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species.

73. The method of claim 59, wherein the bacterial infection is in infection caused by a bacteria selected from the group consisting of *Staphylococcus aureus* (methicillin-resistant and -susceptible), *Staphylococus epidermidis, Staphylococus hemolyticus, Staphylococus saprophyticus, Staphylococus lugdunensis, Staphylococus capitis, Staphylococus caprae, Staphylococus saccharolyticus, Staphylococus simulans, Staphylococus warneri, Staphylococus hominis, Staphylococus intermedius, Staphylococcus pseudointermedius, Staphylococus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Neisseria gonorrhoeae, Neisseria meningitidis, Bacillus anthracis, Bordetella pertussis, Clostridium difficile, Enterococcus faecalis, Enterococcus faecium* and *Corynebacterium diphtheriae*.

74. The method of claim 59, wherein the bacterial infection is an infection caused by *Enterococcus faecalis*.

75. The method of claim 59, wherein the bacterial infection is an infection caused by *Enterococcus faecium*.

* * * * *